(12) United States Patent
Fukuda et al.

(10) Patent No.: US 10,219,769 B2
(45) Date of Patent: Mar. 5, 2019

(54) RADIATION IMAGE PROCESSING APPARATUS, RADIATION IMAGE PROCESSING METHOD, AND RECORDING MEDIUM HAVING RADIATION IMAGE PROCESSING PROGRAM STORED THEREIN

(71) Applicant: FUJIFILM Corporation, Tokyo (JP)

(72) Inventors: Wataru Fukuda, Kanagawa-ken (JP); Junya Morita, Kanagawa-ken (JP)

(73) Assignee: FUJIFILM Corporation, Minato-Ku, Tokyo (JP)

( * ) Notice: Subject to any disclaimer, the term of this patent is extended or adjusted under 35 U.S.C. 154(b) by 73 days.

(21) Appl. No.: 15/428,647

(22) Filed: Feb. 9, 2017

(65) Prior Publication Data

US 2017/0231593 A1 Aug. 17, 2017

(30) Foreign Application Priority Data

Feb. 16, 2016 (JP) ................. 2016-026614

(51) Int. Cl.
| | | |
|---|---|---|
| *G06K 9/00* | (2006.01) | |
| *A61B 6/00* | (2006.01) | |
| *A61B 6/03* | (2006.01) | |
| *G06T 5/50* | (2006.01) | |
| *G06T 7/00* | (2017.01) | |
| *G06T 11/00* | (2006.01) | |

(Continued)

(52) U.S. Cl.
CPC ............ *A61B 6/5258* (2013.01); *A61B 6/025* (2013.01); *A61B 6/032* (2013.01); *A61B 6/4291* (2013.01);
(Continued)

(58) Field of Classification Search
USPC ....... 382/100, 103, 106, 128–134, 154, 162, 382/168, 173, 181, 219, 224, 232, 254,
(Continued)

(56) References Cited

U.S. PATENT DOCUMENTS

| | | | | |
|---|---|---|---|---|
| 8,615,118 | B2* | 12/2013 | Yi ................... | G06T 11/005 |
| | | | | 382/128 |
| 2009/0123052 | A1 | 5/2009 | Ruth et al. | |

(Continued)

FOREIGN PATENT DOCUMENTS

| | | |
|---|---|---|
| GB | 2533632 A | 6/2016 |
| JP | 2012-512669 A | 6/2012 |

(Continued)

OTHER PUBLICATIONS

Communication dated Jun. 22, 2017, from European Patent Office in counterpart application No. 17155198.9.

*Primary Examiner* — Seyed H Azarian
(74) *Attorney, Agent, or Firm* — Sughrue Mion, PLLC

(57) ABSTRACT

A first imaging unit obtains a first radiation image, which is imaged under first imaging conditions. A second imaging unit obtains a plurality of projection images by tomosynthesis imaging under second imaging conditions. A reconstructing unit reconstructs a plurality of projection images to generate a plurality of tomographic images of cross sectional planes of a subject. An image synthesizing unit generates a second radiation image employing the plurality of tomographic images. A subtraction processing unit administers a subtraction process on the first and second radiation images, to generate a subtraction image.

15 Claims, 12 Drawing Sheets

(51) Int. Cl.
  *G06T 11/60* (2006.01)
  *A61B 6/02* (2006.01)
  *A61B 6/04* (2006.01)
(52) U.S. Cl.
  CPC .............. *A61B 6/463* (2013.01); *A61B 6/481* (2013.01); *A61B 6/482* (2013.01); *A61B 6/5223* (2013.01); *A61B 6/5235* (2013.01); *A61B 6/5241* (2013.01); *A61B 6/5282* (2013.01); *G06T 5/50* (2013.01); *G06T 7/0012* (2013.01); *G06T 11/003* (2013.01); *G06T 11/60* (2013.01); *A61B 6/0421* (2013.01); *A61B 6/502* (2013.01); *A61B 6/5205* (2013.01); *G06T 2207/10116* (2013.01); *G06T 2207/20224* (2013.01)
(58) Field of Classification Search
  USPC ...... 382/274, 276, 286–291, 305; 378/4, 15, 378/21, 5, 37
  See application file for complete search history.

(56) References Cited

U.S. PATENT DOCUMENTS

2009/0161818 A1* 6/2009 Sakurai ............... A61N 5/1048
                                                      378/15
2011/0280365 A1* 11/2011 Kojima ................ A61B 6/4241
                                                      378/5
2012/0238870 A1   9/2012 Smith et al.
2013/0044861 A1   2/2013 Muller et al.
2014/0376691 A1* 12/2014 Hoernig ................ G06T 11/006
                                                      378/37
2015/0093013 A1   4/2015 Morita
2015/0110239 A1   4/2015 Muller et al.
2015/0243045 A1*  8/2015 Ra .......................... A61B 6/032
                                                      382/131
2015/0327826 A1  11/2015 Smith et al.
2015/0379711 A1  12/2015 Imai
2016/0007943 A1   1/2016 Hoernig
2016/0012616 A1   1/2016 Hoernig et al.
2016/0235385 A1   8/2016 Enomoto et al.

FOREIGN PATENT DOCUMENTS

| | | |
|---|---|---|
| JP | 2012-166026 A | 9/2012 |
| JP | 2014-14655 A | 1/2014 |
| JP | 2014-507250 A | 3/2014 |
| JP | 2014-207958 A | 11/2014 |
| JP | 2015-89429 A | 5/2015 |

* cited by examiner

| THICKNESS OF BREAST [mm] | SIMPLE IMAGING | | | TOMOSYNTHESIS IMAGING | | |
|---|---|---|---|---|---|---|
| | T/F | TUBE VOLTAGE [kV] | GRID | T/F | TUBE VOLTAGE [kV] | GRID |
| 0-20 | W/Rh | 26 | IN | W/Al | 26 | OUT |
| 20-30 | W/Rh | 27 | IN | W/Al | 28 | OUT |
| 30-40 | W/Rh | 28 | IN | W/Al | 30 | OUT |
| 40-50 | W/Rh | 29 | IN | W/Al | 32 | OUT |
| 50-60 | W/Rh | 30 | IN | W/Al | 34 | OUT |
| 60-70 | W/Rh | 31 | IN | W/Al | 36 | OUT |
| 70-80 | W/Rh | 32 | IN | W/Al | 38 | OUT |
| 80- | W/Rh | 33 | IN | W/Al | 40 | OUT |

| W/Rh | 20 | 40 | 60 | 80 | LUT2 |
|---|---|---|---|---|---|
| 23 | 1.03 | 0.93 | 0.87 | 0.83 | |
| 25 | 0.93 | 0.84 | 0.78 | 0.75 | |
| 27 | 0.90 | 0.81 | 0.76 | 0.72 | |
| 29 | 0.87 | 0.79 | 0.73 | 0.69 | |
| 31 | 0.85 | 0.76 | 0.70 | 0.65 | |
| 33 | 0.82 | 0.72 | 0.65 | 0.60 | |
| 35 | 0.78 | 0.68 | 0.60 | 0.54 | |

THICKNESS [mm]

TUBE VOLTAGE [kV]

TGj

RADIATION IMAGE PROCESSING APPARATUS, RADIATION IMAGE PROCESSING METHOD, AND RECORDING MEDIUM HAVING RADIATION IMAGE PROCESSING PROGRAM STORED THEREIN

CROSS REFERENCE TO RELATED APPLICATIONS

The present application claims priority under 35 U.S.C. § 119 to Japanese Patent Application No. 2016-026614 filed on Feb. 16, 2016. The above application is hereby expressly incorporated by reference, in its entirety, into the present application.

BACKGROUND

The present disclosure is related to a radiation image processing apparatus, a radiation image processing method, and a radiation image processing program that generates subtraction images from two dimensional images obtained by simple imaging and tomographic images obtained by tomosynthesis imaging.

Recently, tomosynthesis imaging has been proposed for radiation image obtaining apparatuses that employ radiation such as X rays and gamma rays. Tomosynthesis imaging obtains images by irradiating radiation onto a subject from a plurality of radiation source positions by moving a radiation source, and generates a tomographic image in which a desired cross sectional plane is emphasized, from a plurality of projection images obtained by the imaging operations, in order to observe an afflicted portion in greater detail. In tomosynthesis imaging, the radiation source may be moved parallel to a radiation detector or moved along a circular or elliptical trajectory according to the characteristics of an imaging apparatus or necessary tomographic images. The subject is imaged at a plurality of radiation source images to obtain a plurality of projection images. A tomographic image is generated by reconstructing the projection images by an inverse projection method such as the simple inverse projection method or a filtered inverse projection method. Structures that overlap in the depth direction in which cross sectional planes are arranged can be separated, by generating such tomographic images at a plurality of cross sectional planes within the subject. For this reason, it becomes possible to detect lesions, which had been difficult to detect within two dimensional images obtained by conventional simple imaging. Note that simple imaging is an imaging method in which radiation is irradiated onto a subject onetime, and a single two dimensional image, which is a transmission image of the subject, is obtained.

Meanwhile, there is a problem in tomosynthesis imaging that reconstructed tomographic images become blurred due to the influence of mechanical errors of an imaging apparatus, body movement of a subject caused by temporal differences among imaging operations at each of a plurality of radiation source positions, etc. If a tomographic image is blurred, it will become difficult for lesions such as fine calcifications, which are effective in early diagnosis of breast cancer, to be detected, in the case that the subject is a breast. For this reason, simple imaging is also performed in the case that tomosynthesis imaging is performed, to obtain both tomographic images and two dimensional images.

For this reason, radiation imaging apparatuses for imaging breasts (called mammography apparatuses) that perform both tomosynthesis imaging and simple imaging with breasts maintained in a compressed state have been proposed (refer to PCT Japanese Publication No. 2014-507250 and Japanese Unexamined Patent Publication No. 2012-166026).

In addition, subtraction processes are performed in mammography, in order to facilitate discrimination of lesions. Here, subtraction processes refer to a process in which an image corresponding to a difference in a plurality of radiation images imaged under different imaging conditions is obtained. Specifically, a subtraction process is administered for each corresponding pixel within the plurality of images, to emphasize or extract a specific portion of the subject within the radiation images, that is, to obtain a subtraction image.

There are basically two types of subtraction processes which are performed in mammography. One type of subtraction process is temporal subtraction. In temporal subtraction, an image, in which blood vessels of a breast are not emphasized, is subtracted from an image, in which the blood vessels of the breast are emphasized by imaging after injecting a contrast agent into the breast from a vein, to extract the blood vessel portions. The other type of subtraction process is energy subtraction. Energy subtraction utilizes the fact that contrast agents have different radiation absorption rates with respect to radiation having different energies. In energy subtraction, radiation having different energies are irradiated onto a breast after a contrast agent is injected, to obtain radiation images having different energies. The plurality of radiation images are weighted appropriately and differences among the radiation images are calculated, to extract the blood vessel portions of the breast. In addition, there are cases in which radiation is irradiated onto a breast at temporal intervals after a contrast agent is injected to obtain a plurality of radiation images. In such cases, the plurality of radiation images are weighted appropriately and differences among the radiation images are calculated, to ascertain the spread of the contrast agent through the blood vessel portions of the breast.

In many cases, breast cancer progresses by the blood vessel walls being weak and newly formed blood vessels that spread randomly toward the periphery increasing. The increased newly formed blood vessels increase transmissivity and are serpentine, different from normal blood vessels. Accordingly, the increased newly formed blood vessels can be extracted by employing subtraction images, thereby facilitating detection of breast cancer.

For this reason, a technique in which two radiation images to be subjected to a subtraction process are obtained to generate a subtraction image in addition to obtaining tomographic images by tomosynthesis imaging, and the subtraction image and the tomographic images are displayed has been proposed (refer to PCT Japanese Publication No. 2014-507250). In addition, a CE-DBT (Contrast Enhanced Digital Breast Tomosynthesis) technique that obtains radiation images to be subjected to subtraction processes at each radiation source position when performing tomosynthesis imaging has also been proposed (refer to Japanese Unexamined Patent Publication No. 2012-166026).

When obtaining radiation images, a scattered radiation removing grid (hereinafter, simply referred to as "grid") is utilized when performing imaging, in order to prevent decreases in contrast due to the influence of scattered radiation which is generated within subjects. Meanwhile, tomosynthesis imaging performs imaging operations by irradiating radiation onto a subject from each of a plurality of radiation source positions. Therefore, the incident angle of radiation with respect to a radiation detector differs for each radiation source position. For this reason, if a grid is employed when performing imaging operations, vignetting occurs by the radiation being cut off by the grid depending on the radiation source position, and the amount of radiation that reaches the radiation detector will decrease. Accordingly, a grid is not employed when performing tomosynthesis imaging.

In addition, in the case that tomosynthesis imaging is performed, imaging operations are performed while moving a radiation source. Therefore, it is necessary to set the irradiation time of radiation onto a subject for each imaging operation to be as short as possible, to prevent blurring of projection images. Meanwhile, if the amount of irradiation time is set to be short, the amount of radiation which is irradiated onto the subject also decreases, resulting in the amount of radiation that reaches a radiation detector also decreasing. For this reason, high energy radiation that more readily passes through objects is employed in tomosynthesis imaging, in order to increase the amount of radiation that reaches a radiation detector with a minimal radiation dosage.

SUMMARY

However, the radiation dosage irradiated onto a subject will increase if tomosynthesis imaging, simple imaging, and imaging for subtraction processes are performed. For this reason, PCT Japanese Publication No. 2014-507250 proposes to generate two dimensional images corresponding to those obtained by simple imaging from projection images obtained by tomosynthesis imaging. However, the amount of radiation which is irradiated during each tomosynthesis imaging operation is small, and therefore the S/N ratio of projection images is poor. Therefore, the image quality of subtraction images will deteriorate if two dimensional images which are generated from such projection images are employed.

The present disclosure has been developed in view of the foregoing circumstances. The present disclosure enables radiation dosages irradiated onto subjects to be reduced and the image quality of subtraction images to be improved when generating subtraction images.

A radiation image processing apparatus of the present disclosure comprises:

a first image obtaining means configured to obtain a first radiation image which is imaged by irradiating radiation onto a subject from a first radiation source position under first imaging conditions;

a second image obtaining means configured to obtain a plurality of projection images corresponding to each of a plurality of radiation source positions by moving a radiation source relative to a detecting means and irradiating the subject with radiation from the plurality of radiation source positions under second imaging conditions;

a reconstructing means configured to generate a plurality of tomographic images for each of a plurality of cross sectional planes within the subject by reconstructing the plurality of projection images;

an image synthesizing means configured to generate a second radiation image employing the plurality of tomographic images; and a subtracting means configured to administer subtraction processes on the first radiation image and the second radiation image to generate a subtraction image.

The expression "moving a radiation source relative to a detecting means" refers to a case in which only the radiation source is moved, a case in which only the detecting means is moved, and a case in which both the radiation source and the detecting means are moved.

The expression "generate a second radiation image employing the plurality of tomographic images" is not limited to cases in which only the plurality of tomographic images are employed to generate the second radiation image, but also includes cases in which pieces of information other than the plurality of tomographic images, for example, the projection images, are employed to generate the second radiation image.

The "subtraction processes" may refer to temporal subtraction or energy subtraction. In the case of temporal subtraction, the first radiation image may be obtained by imaging employing a contrast agent, and the plurality of projection images may be obtained by imaging without employing the contrast agent. Conversely, the first radiation image may be obtained by imaging without employing a contrast agent, and the second images may be obtained by imaging employing the contrast agent. As a further alternative, both the first radiation image and the plurality of projection images may be obtained by imaging employing a contrast agent, in order to view the spread of the contrast agent over time.

Note that in the radiation image processing apparatus of the present disclosure, the image synthesizing means may generate the second radiation image by combining a plurality of tomographic images.

In addition, the radiation image processing apparatus of the present disclosure may further comprise an image quality correction processing means configured to administer image quality correcting processes that compensate for differences in the image qualities of the first radiation image and the second radiation image, based on differences between the first imaging conditions and the second imaging conditions.

In this case, the image correction processes may include at least one of: a scattered radiation removing process that removes scattered radiation components included in radiation which has passed through the subject from the plurality of projection images in the case that imaging is performed employing the second imaging conditions; and a radiation quality correcting process that corrects differences in contrast between the first radiation image and the plurality of projection images, due to differences in the radiation quality of the first imaging conditions and the radiation quality of the second imaging conditions.

Additionally in this case, the image quality correcting processes may include the scattered radiation removing process and the radiation quality correcting process.

Further, in this case, the image quality correction processing means may administer the scattered radiation removing process before administering the radiation quality correcting process.

In addition, in the radiation image processing apparatus of the present disclosure, the reconstructing means may comprise:

a pixel value projecting means configured to project pixel values of the projection images onto coordinate positions on cross sectional planes of the subject while maintaining the pixel values of the projection images, based on the positional relationship between the radiation source position and the detecting means at the time of imaging; and a pixel value calculating means configured to generate the tomographic images of the cross sectional planes by calculating the pixel value at a coordinate position of interest, based on a plurality of pixel values of the projection images which are projected within a predetermined range having the coordinate position of interest within the cross sectional planes as a reference position.

Note that in the case that the image quality correcting processes are administered, the projection images are those in which the image quality correcting processes have been administered.

In this case, the pixel value calculating means may calculate the pixel value at the coordinate position of interest by performing regression analysis on the pixel values of the projection image which are projected onto the cross sectional plane.

Note that the projection images and the tomographic images of the cross sectional planes are constituted by pluralities of pixels which are discretely arranged two dimensionally at a predetermined sampling interval. Pixels are arranged at lattice points which are the predetermined sampling interval. In the present disclosure, the expression "pixel position" refers to the positions of lattice points at which pixel values are arranged to form images. Meanwhile, the expression "coordinate position" not only includes lattice points at which pixel values are arranged to form images, that is, the pixel positions, but also positions among the lattice points at which pixel values that form images are not arranged. Accordingly, the "coordinate position" includes not only the pixel positions, but also positions among the pixel positions.

The expression "while maintaining the pixel values of the projection images" means that the pixel values of the projection images are not changed. Note that in the present disclosure, there are cases in which pixel values of pixel positions of the projection images cannot be projected onto the coordinate positions of the cross sectional planes. That is, depending on the positional relationship between the radiation source position and the detecting means, the pixel values of the projection images corresponding to the coordinate positions on the cross sectional lanes are not present at the pixel positions of the projection images, but are present at coordinate positions among the pixel positions. In such cases, the pixel values of the projection images which are projected onto the coordinate positions of the cross sectional planes may be calculated by interpolating the pixel values at pixel positions about the periphery of the coordinate position, for example. In such cases as well, the pixel values which are calculated by interpolation are pixel values of the projection images. Therefore, the pixel values of the projection images which are calculated by interpolation may be maintained and projected onto coordinate positions on the cross sectional planes.

The expression "coordinate position of interest within the cross sectional plane" refers to a coordinate position which is a target for which a pixel value is calculated when generating a tomographic image of a cross sectional plane. Accordingly, a tomographic image of a cross sectional plane can be generated by successively changing the coordinate position of interest within the cross sectional plane and calculating the pixel value at the coordinate position of interest.

The expression "a predetermined range having the coordinate position of interest within the cross sectional planes as a reference position" refers to a range that includes the coordinate position of interest and a predetermined number of coordinate positions or pixel positions about the periphery of the coordinate position of interest. For example, a 3×3 range of coordinate positions or pixel positions having the coordinate position of interest at its center, a 5×5 range of coordinate positions or pixel positions having the coordinate position of interest at its center, etc. may be the predetermined range having the coordinate position of interest as a reference position. Note that the size of the predetermined range may be a fixed value, or may be changed to arbitrary values by operator input.

"Regression analysis" is a statistical technique for analyzing the relationships among multiple variables. Here, assume that an observed value at an observation point is observed as a true value with noise included therein. Regression analysis is a technique for solving the inverse problem of deriving the true value at various observation points by regression employing the least square method, the moving average method, and kernels, etc. In the present disclosure, the coordinate position on the cross sectional plane onto which a pixel value of a projection image is projected is designated as an observation point, and the pixel value of the observation point is designated as an observed value. The pixel value at a coordinate position of interest is designated as a true value, which is calculated by regression analysis.

In addition, in the radiation image processing apparatus of the present disclosure, the image synthesizing means may correct the pixel positions of a plurality of tomographic images such that they are those that would be the pixel positions for a case in which radiation is irradiated onto the subject from the first radiation source position, to generate the second radiation image.

In addition, in the radiation image processing apparatus of the present disclosure, the image synthesizing means may generate the second radiation image such that it is of the same size as the first radiation image.

In addition, the radiation image processing apparatus of the present disclosure may further comprise a display control means for displaying the plurality of tomographic images on a display means.

In this case, the display control means may display the plurality of tomographic images such that an abnormal portion which is specified by the subtraction image is emphasized.

In addition, in this case, the display control means may display the subtraction image overlapped with each of the plurality of tomographic images.

In addition, in the radiation image processing apparatus of the present disclosure, at least one of the first radiation image and the plurality of projection images may be obtained by imaging operations that employ a contrast agent.

A radiation image processing method of the present disclosure comprises:

obtaining a first radiation image which is imaged by irradiating radiation onto a subject from a first radiation source position under first imaging conditions;

obtaining a plurality of projection images corresponding to each of a plurality of radiation source positions by moving a radiation source relative to a detecting means and irradiating the subject with radiation from the plurality of radiation source positions under second imaging conditions;

generating a plurality of tomographic images for each of a plurality of cross sectional planes within the subject by reconstructing the plurality of projection images;

generating a second radiation image employing the plurality of tomographic images; and administering subtraction processes on the first radiation image and the second radiation image to generate a subtraction image.

Note that the radiation image processing method of the present disclosure may be provided as a program to be executed by a computer.

According to the present disclosure, a plurality of projection images are reconstructed to generate a plurality of tomographic images, and a second radiation image is generated based on information of the plurality of tomographic images. Here, the tomographic images are generated from a plurality of projection images, and therefore the amount of noise therein is less than that within the projection images. For this reason, the amount of noise in the second radiation image is also reduced. Accordingly, a subtraction image having high image quality, in which the amount of noise is reduced, can be generated, by executing a subtraction process on the first radiation image and the second radiation image. In addition, the second radiation image is generated based on information of the plurality of tomographic images. Therefore, the number of imaging operations necessary to generate the subtraction image can be decreased. Thereby, the radiation dosage irradiated on the subject can also be decreased.

DETAILED DESCRIPTION OF THE PREFERRED EMBODIMENTS

Figure 1:
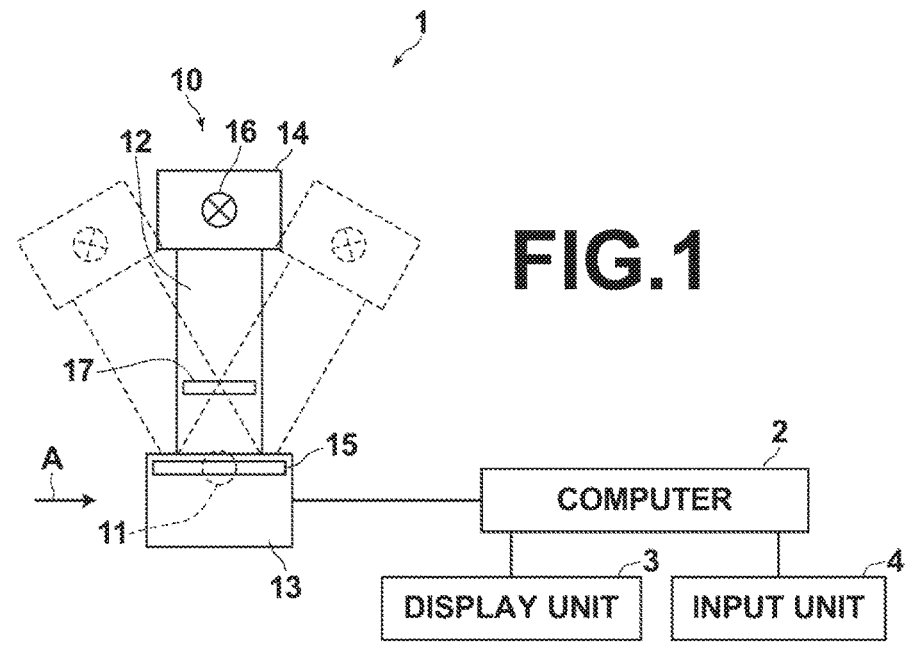
FIG. 1 is a diagram that schematically illustrates the configuration of a radiation image obtaining apparatus to which a radiation image processing apparatus according to a first embodiment of the present disclosure is applied.
Figure 2:
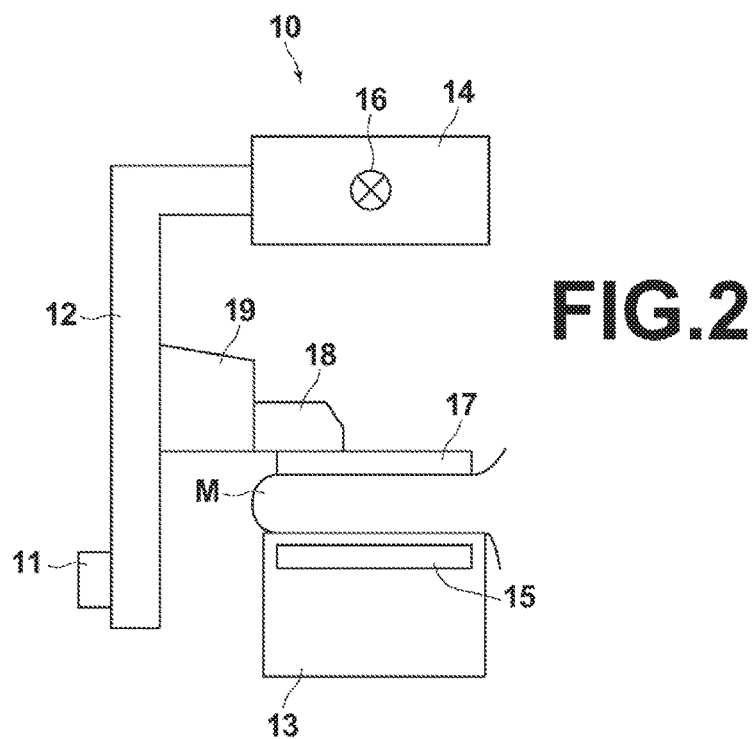
FIG. 2 is a diagram of the radiation image obtaining apparatus as viewed from the direction of arrow A in FIG. 1.

Hereinafter, embodiments of the present disclosure will be described with reference to the drawings. FIG. 1 is a diagram that schematically illustrates the configuration of a radiation image obtaining apparatus to which a radiation image processing apparatus according to a first embodiment of the present disclosure is applied, and FIG. 2 is a diagram of the radiation image obtaining apparatus as viewed from the direction of arrow A in FIG. 1. A radiation image obtaining apparatus 1 images a breast M, which is a subject, from a plurality of radiation source positions having different imaging directions to generate a plurality of radiation images, in order to generate tomographic images by performing tomosynthesis imaging of a breast. That is, the radiation image obtaining apparatus 1 is a mammography apparatus that generates a plurality of projection images. As illustrated in FIG. 1, the radiation image obtaining apparatus 1 includes an imaging unit 10, a computer 2 connected to the imaging unit 10, a display unit 3, and an input unit 4 connected to the computer 2. The radiation image obtaining apparatus 1 according to the present embodiment also performs simple imaging as will be described later, to acquire two dimensional images, which are transmission images, of the breast M. In the present embodiment, simple imaging and tomosynthesis imaging are performed by injecting a contrast agent into the breast M.

The imaging unit 10 includes an arm unit 12 connected to a base (not shown) by a rotatable shaft 11. An imaging base 13 is attached to one end of the arm unit 12, and a radiation irradiating section 14 is attached to the other end of the arm unit 12 so as to face the imaging base 13. The arm unit 12 is configured so as to be able to rotate only at the end portion to which the radiation irradiating unit 14 is attached, so that it is possible to rotate only the radiation irradiation unit 14 with the imaging base 13 being fixed. Note that rotation of the arm unit 12 is controlled by the computer 2.

A radiation detector 15 such as a flat panel detector is provided within the imaging base 13. A charge amplifier for converting the charge signal read from the radiation detector 15 into a voltage signal, a correlated double sampling circuit for sampling a voltage signal output from the charge amplifier, and a circuit board provided with an A/D converter for converting the digital signal into a digital signal and the like are also provided within the imaging base 13. The radiation detector 15 corresponds to a detecting means.

The radiation detector 15 can repeatedly record and read out radiation images. It is possible to use a so called direct type radiation detector that directly receives irradiation of radiation and generates electrical charges, or a so called indirect type radiation detector which converts radiation into visible light, and then converts the visible light into electrical charge signals. In addition, as preferred methods for reading out radiation image signals, there are a so called TFT readout method in which a radiation image signal is read out by turning a thin film transistor (TFT) switch ON and OFF, and a so called light readout method in which radiation image signals are read out by irradiating readout light. However, the present disclosure is not limited to these readout methods, and other methods may be employed.

An X ray source 16, which is a radiation source, is housed inside the radiation irradiation unit 14. The timings at which X rays are irradiated as radiation from the X ray source 16 and X ray generating conditions in the X ray source 16, that is, the material of the anode and the filter, as well as imaging conditions such as the tube voltage and the irradiation time, are controlled by the computer 2.

Further, a compression plate 17 disposed above the imaging base 13 to press the breast M to compress it, a support section 18 for supporting the compression plate 17, and a moving mechanism 19 for moving the support section 18 in the vertical direction of FIGS. 1 and 2, are provided on the arm unit 12. Note that the distance between the compression plate 17 and the imaging base 13, that is, the compression thickness, is input to the computer 2.

The display unit 3 is a display device such as a CRT or a liquid crystal monitor, and displays projection images, two dimensional images, tomographic images and subtraction images, which are obtained as will be described later. In addition, the display unit 3 also displays messages and the like which are necessary for operations. Note that the display unit 3 may include a built in speaker that outputs sound.

The input unit 4 comprises input devices such as a keyboard, a mouse and a touch panel, and receives operations of the radiation image obtaining apparatus 1 which are input by an operator. Also, the input unit 4 accepts various pieces of information necessary for performing tomosynthesis photographing, such as imaging conditions and commands to correct information. In the present embodiment, each part of the radiation image obtaining apparatus 1 operates according to the information input by the operator from the input unit 4.

A radiation image processing program is installed in the computer 2. In the present embodiment, the computer may be a work station or a personal computer which the operator directly operates, or may be a server computer connected to a work station or a personal via a network. The radiation image processing program is recorded and distributed on a recording medium such as a DVD (Digital Versatile Disc), CD-ROM (Compact Disc Read Only Memory), etc., and installed on the computer from the recording medium. Alternatively, the radiation image processing program is stored in a storage device or a network storage of a server computer connected to a network in an accessible state from the exterior, downloaded to a computer in response to a request, and installed.

Figure 3:
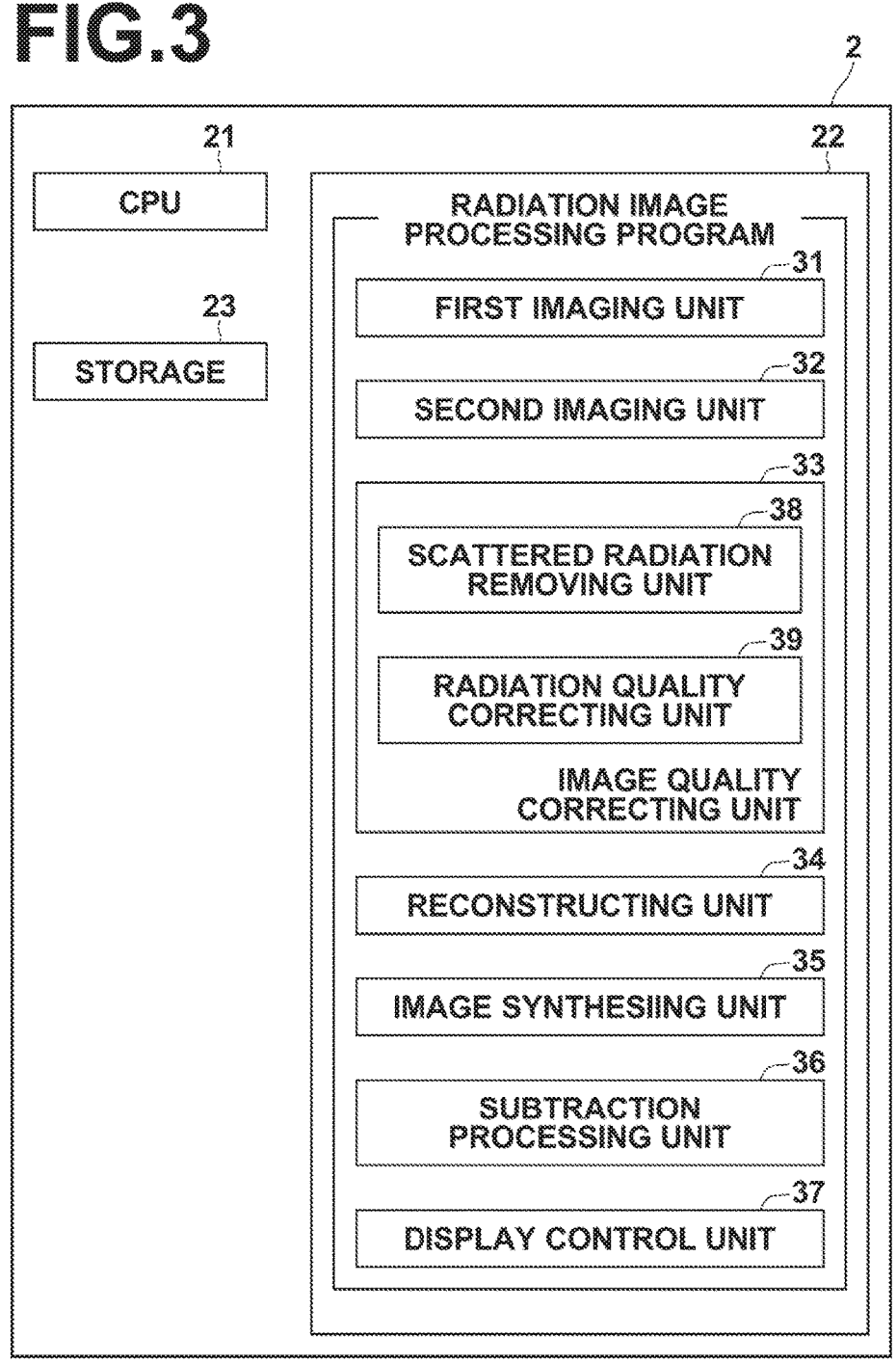
FIG. 3 is a diagram that schematically illustrates the configuration of the radiation image processing apparatus of the first embodiment, which is realized by installing a radiation image processing program in a computer.

FIG. 3 is a diagram that schematically illustrates the configuration of the radiation image processing apparatus of the first embodiment, which is realized by installing the radiation image processing program in the computer 2. As illustrated in FIG. 3, the radiation image processing apparatus includes a CPU (Central Processing Unit) 21, a memory 22, and a storage 23, as components of a standard computer configuration.

The storage 23 includes a storage device such as a hard disk or an SSD (Solid State Drive), and stores various types of data, including programs for driving each part of the radiation image obtaining apparatus 1, and the radiation image processing program. In addition, projection images acquired by tomosynthesis imaging, two dimensional images acquired by simple imaging, tomographic images, synthesized two dimensional images, and subtraction images, which are generated as will be described later, are also stored in the storage 23. Various tables to be described later are also stored in the storage 23.

The memory 22 temporarily stores programs and the like which are stored in the storage 23 so as to cause the CPU 21 to execute various processes. The radiation image processing program defines processes to be executed by the CPU 21, which are: a first radiation imaging process that acquires a two dimensional image by irradiating X rays onto a breast M as a subject from a first radiation source position, under first imaging conditions; a second radiation imaging process that acquires a plurality of projection images corresponding to each of a plurality of radiation source positions, by moving the X ray source 16 relative to the radiation detector 15 and irradiating X rays onto the breast M at the plurality of radiation source positions under second imaging conditions; an image quality correcting process that administers image quality correcting processes onto the projection images to compensate for differences in image quality between the projection images and the two dimensional image, due to differences between the first imaging conditions and the second imaging conditions; a reconstructing process that generates a plurality of tomographic images of a plurality of cross sectional planes within the breast M by reconstructing the projection images which have undergone the image correction processes and the two dimensional image; an image synthesizing process for generating a synthesized two dimensional image employing the plurality of tomographic images; a subtraction process that generates a subtraction image by administering a subtraction process on the two dimensional image and the synthesized two dimensional image; and a display control process that causes the subtraction image, the two dimensional images, and the tomographic images to be displayed by the display unit 3.

By the CPU 21 executing these processes according to the radiation image processing program, the computer 2 functions as a first imaging unit 31, a second imaging unit 32, an image quality correcting unit 33, a reconstruction unit 34, an image synthesizing unit 35, a subtraction processing unit 36, and a display control unit 37. Note that the computer 2 may include processors that respectively perform each of a first imaging process, a second imaging process, an image quality correcting process, a reconstruction process, an image synthesizing process, a subtraction process, and a display control process.

Figure 4:
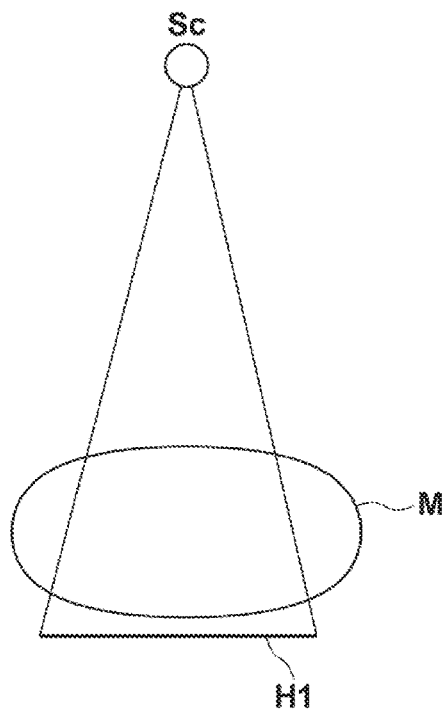
FIG. 4 is a diagram for explaining obtainment of a two dimensional image.
Figure 5:
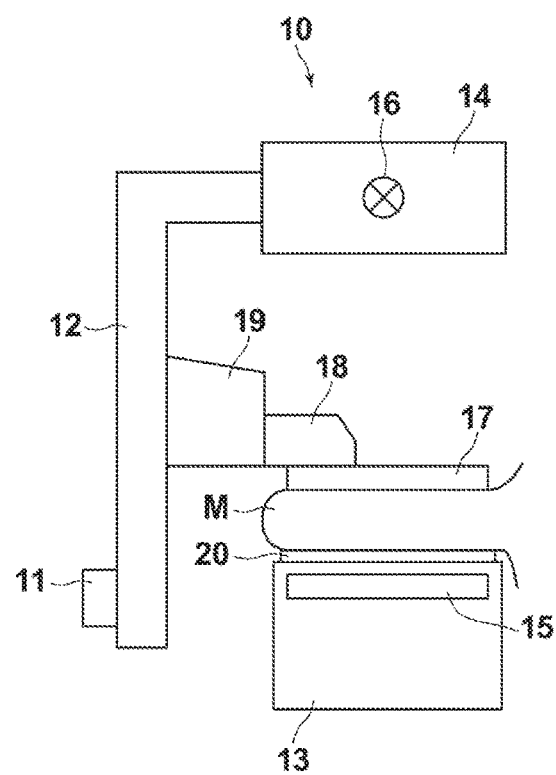
FIG. 5 is a diagram of the radiation image obtaining apparatus as viewed from the direction of arrow A in FIG. 1 when obtaining the two dimensional image.

The first imaging unit 31 acquires a two dimensional image H1. The two dimensional image H1 corresponds to the first radiation image. FIG. 4 is a diagram for explaining obtainment of the two dimensional image H1. As illustrated in FIG. 4, the first imaging unit 31 causes the X ray source 16 to move to a first radiation source position Sc by rotating the arm unit 12 around the rotatable shaft 11, and X rays are irradiated onto the breast M as a subject under the first imaging conditions for simple imaging at the radiation source position Sc. The X rays which are transmitted through the breast M are detected by the radiation detector 15, and the two dimensional image H1 is obtained as a two dimensional radiation image. A scattered radiation removal grid 20 (hereinafter, simply referred to as "grid") for removing scattered radiation transmitted through the breast M is provided between the breast M and the radiation detector 15. When tomosynthesis imaging is performed, the grid 20 is not provided, as illustrated in FIG. 2. Further, when the grid 20 is provided, the compression thickness is the distance between the upper surface of the grid 20 and the compression plate 17.

Figures 6, 7:
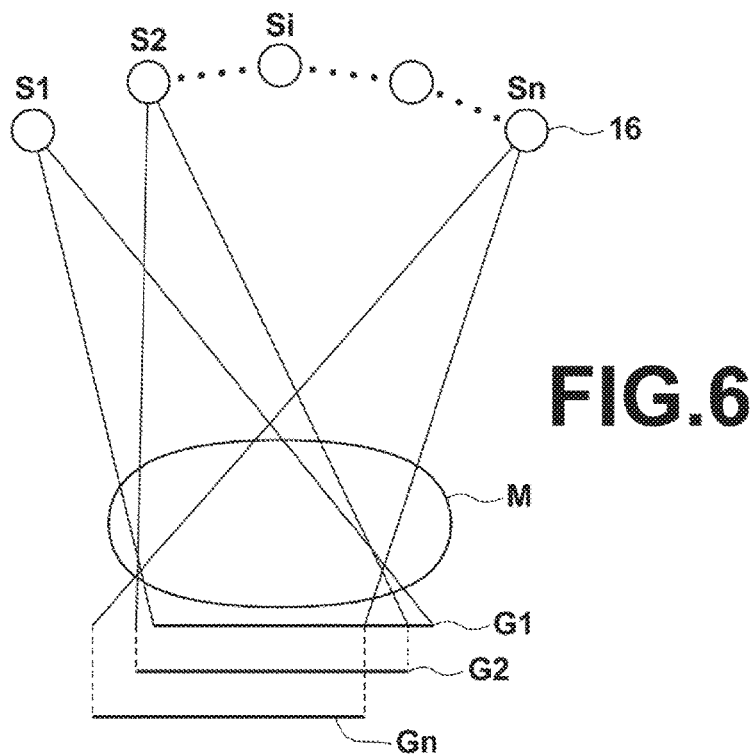
FIG. 6 is a diagram for explaining obtainment of a projection image.
FIG. 7 is a diagram that illustrates a table that lists imaging conditions.

The second imaging unit 32 moves the X ray source 16 by rotating the arm unit 12 around the rotatable shaft 11, X rays are irradiated onto the breast M as a subject according to the second imaging conditions at a plurality of radiation source positions due to the movement of the X ray source, the X rays transmitted through the breast M are detected by the radiation detector 15, and a plurality of projection images Gi (i=1 to n, n is the number of radiation source positions). FIG. 6 is a diagram for explaining obtainment of the projection images Gi. As illustrated in FIG. 6, the X ray source 16 is moved to each radiation source position S1, S2, . . . , Sn, and the X ray source 16 is driven at each radiation source position to irradiate the breast M with X rays. By detecting the X rays transmitted through the breast M with the radiation detector 15, the projection images G1, G2, . . . , Gn are acquired corresponding to the respective radiation source positions S1 to Sn. The plurality of obtained projection images Gi are stored in the storage 23. A plurality of projection images Gi may be obtained by a program separate from the radiation image processing program and stored in the storage 23. In this case, the second imaging unit 32 reads out the plurality of projection images Gi stored in the storage 23 from the storage 23 for the image quality correcting process and the reconstruction processing.

Next, the first and second imaging conditions will be described. The X ray source 16 includes a filament for outputting an electron beam, a target for generating X rays by the electron beam colliding therewith, and a filter for adjusting the energy spectrum of X rays. The target has a plurality of different anode materials, for example Mo, Rh and W, which are provided to be selectable. The filter has a plurality of different substances, for example Mo, Rh, W and Al, which are provided to be selectable.

Imaging conditions are conditions for obtaining an appropriate radiation image by adjusting the energy spectrum (radiation quality) of X rays to be irradiated onto the breast M. For example, the imaging conditions include the type of target constituting the X ray source 16, the type of filter, X ray generating conditions including a tube voltage applied between the filament and the target, and grid conditions that indicate the presence or absence of the grid 20. It should be noted that a mAs value (tube current×radiation irradiation time) may be included as an imaging condition. Also, in the case that a grid is employed, if the type of the grid, that is, a grid ratio, a grid density, whether the grid is of the convergence type or parallel type, the convergence distance in the case that the grid is of the convergent type, and an interspace material (aluminum, fiber, bakelite, etc.) differs, the characteristics of the grid to be described later will also differ. Therefore, the imaging conditions also include grid information that indicates the type of the grid.

In the present embodiment, a table of imaging conditions for tomosynthesis photography and simple photography is stored in the storage 23. FIG. 7 is a diagram that illustrates a table of imaging conditions. As illustrated in FIG. 7, the table LUT 1 for imaging conditions prescribes imaging conditions corresponding to a plurality of breast thicknesses. Specifically, T/F, which indicates the type of the target and the filter, the tube voltage, and the presence or absence of the grid are set. Note that IN indicates that a grid is employed and OUT indicates that a grid is not employed. By referring to the table LUT 1, for example, when the thickness of the breast is 45 mm and T/F is W/Rh (target is W, filter is Rh), and the tube voltage is 29 kV as first imaging conditions during simple imaging. During tomosynthesis imaging, T/F is W/Al (target is W, filter is Al), tube voltage is high voltage 32 kV, and no grid is set as second imaging conditions. Since the tube voltage is higher for tomosynthesis imaging, the breast M is irradiated with higher energy X rays during tomosynthesis imaging than during simple imaging. Hereafter, simple imaging will be described as being performed with low energy X rays, and tomosynthesis imaging will be described as being performed with high energy X rays. The set first and second imaging conditions are stored in the storage 23.

Figure 8:
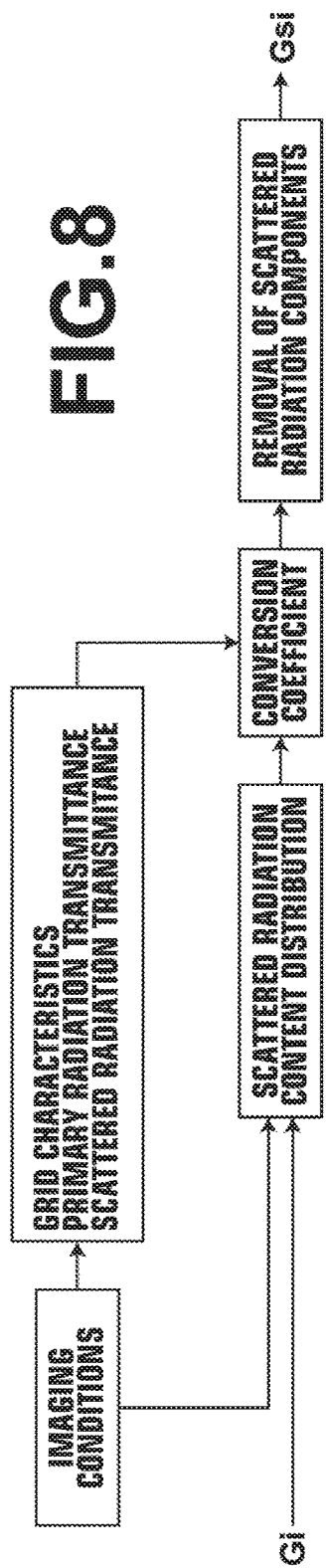
FIG. 8 is a block diagram for explaining a scattered radiation removing process.

The image quality correcting unit 33 includes a scattered radiation removing unit 38 and a radiation quality correcting unit 39. The scattered radiation removing unit 38 administers a scattered radiation removing process that removes scattered radiation components included in the X rays which are transmitted through the breast M from the projection images Gi during tomosynthesis imaging using the second imaging conditions, from the plurality of projection images Gi. In the present embodiment, the scattered radiation removing processing is performed using the methods described in, for example, Japanese Unexamined Patent Publication Nos. 2014-207958 and 2015-089429. Hereinafter, the scattered radiation removing process will be described. FIG. 8 is a block diagram for explaining the scattered radiation removing process.

First, the scattered radiation removing unit 38 obtains grid characteristics from the grid information included in the first imaging conditions which are stored in the storage 23. The obtained grid characteristics are the scattered radiation transmittance Ts of the grid 20 used at the time of simple imaging and the transmittance (primary radiation transmittance) Tp of primary radiation which passes through the breast M and is directly irradiated onto the radiation detector 15. In the present embodiment, the table in which the grid information and the grid characteristics are associated with each other is stored in the storage 23, and the scattered radiation removing unit 38 refers to this table and acquires the grid characteristics from the grid information.

In addition, the scattered radiation removing unit 38 calculates a primary radiation image and a scattered radiation image from the distribution T (x, y) of the subject thickness in each projection image Gi according to equations (1) and (2) below. The scattered radiation content distribution S (x, y) is calculated from the primary radiation image and the scattered radiation image according to formula (3).

$$Icp(x,y)=Io(x,y)\times\exp(-\mu\times T(x,y)) \qquad (1)$$

$$Ics(x,y)=Io(x,y)*S\sigma(T(x,y)) \qquad (2)$$

$$S(x,y)=Ics(x,y)/(Ics(x,y)+Icp(x,y)) \qquad (3)$$

Here, (x, y) is the coordinate of a pixel position within the projection image Gi, Icp (x, y) is a primary radiation image at the pixel position (x, y), Ics (X, Y) is an incident radiation dosage to the surface of the subject's body at the pixel position (x, y), μ is the radiation attenuation coefficient of the breast M as the subject, and Sσ (T (x, y)) is a convolution kernel that represents the characteristics of scattering according to the subject thickness at the pixel position (x, y). In the present embodiment, the distribution T (x, y) of the subject thickness may be the compression thickness at the time of tomosynthesis imaging. The compression thickness is constant in the region of the breast M included in the projection image Gi. Therefore, in the present embodiment, calculation of the scattered radiation content distribution S (x, y) can be performed with a comparatively small amount of calculations. In addition, * in equation (2) is an operator representing a convolution operation. Further, Sσ (T (x, y)) can be experimentally obtained according to imaging conditions. In the present embodiment, a table in which various imaging conditions are associated with Sσ (T (x, y)) is stored in the storage 23, and Sσ (T X, y)) is derived from the first imaging conditions by referring to this table.

Then, the scattered radiation removing unit 38 calculates a conversion coefficient R (x (x, y)) for transforming the projection images Gi from the scattered radiation transmittance Ts, the primary radiation transmittance Tp and the scattered radiation content distribution S(x, y) by Formula (4) below. Further, the scattered radiation removing unit 38 multiplies the pixel value of each pixel of the projection image Gi by the conversion coefficient R (x, y) according to Formula (5) below, thereby removing the scattered radiation component from the projection images Gi, to acquire scattered radiation removing processed projection images Gsi.

$$R(x,y)=S(x,y)\times Ts+(1-S(x,y))\times Tp \quad (4)$$

$$Gs(x,y)=R(x,y)\times G(x,y) \quad (5)$$

Note that the projection images Gi may be decomposed into a plurality of frequency bands, and calculation of conversion coefficients and multiplication of conversion coefficients may be performed for each frequency band. In this case, the projection image of each frequency band multiplied by the conversion coefficient is frequency synthesized, thereby acquiring the scattered radiation removing processed projection images Gsi.

The radiation quality correcting unit 39 administers a radiation quality correcting process to correct the contrast difference between the projected images Gi and the two dimensional image H1 due to the difference between the quality of the first imaging conditions and the quality of the second imaging conditions. Note that the radiation quality correcting process is performed on the projection images Gsi which have undergone the scattered radiation removing process. The radiation quality correcting process is performed by using the method described in, for example, Japanese Unexamined Patent Publication No. 2014-014655. The radiation quality correcting process will be described below. First, the radiation quality correcting unit 39 acquires first contrast information representing the contrast of the projection images Gsi. Here, in the present embodiment, a contrast table which is a three-dimensional table that defines the thicknesses of a plurality of breasts M and the contrast corresponding to a plurality of tube voltages is stored for each combination of the target and the filter used during imaging is stored. The radiation quality correcting unit 39 refers to the contrast table, and acquires the first contrast information representing the contrast of the projection images Gsi, based on the second imaging conditions and the thickness of the breast M.

Figures 9, 10:
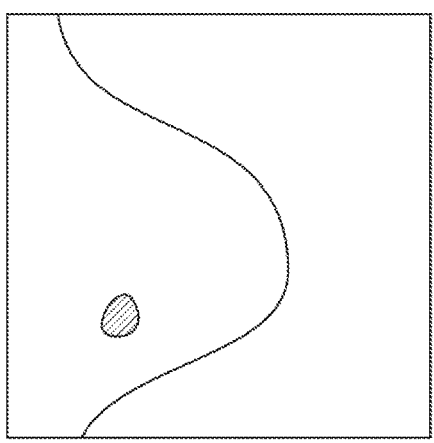
FIG. 9 is a diagram that illustrates a contrast table.
FIG. 10 is a diagram that illustrates a state in which a tomographic image is displayed with a portion that corresponds to an abnormal portion having color added thereto.

FIG. 9 is a diagram that illustrates a contrast table, which is a table that defines contrast information. As illustrated in FIG. 9, the contrast table LUT 2 is a three dimensional table defining contrasts corresponding to the thicknesses of a plurality of breasts, a plurality of tube voltages, and a plurality of mammary gland/fat ratios, for each combination of targets and filters. In the contrast table LUT 2 illustrated in FIG. 9, the contrast corresponding to the thicknesses of a plurality of breasts and a plurality of tube voltages is defined for a case in which the ratio of mammary fat is 50% when the target and filter combination is W/Rh. In FIG. 9, although the contrast table LUT 2 is shown in two dimensions, it is actually a three dimensional table in which the two dimensional table illustrated in FIG. 9 is defined corresponding to a plurality of mammary gland/fat ratios. Further, as illustrated in FIG. 9, for example, the contrast table LUT 2 discretely defines breast thicknesses at intervals of 20 mm, tube voltages at 2 kV intervals, and mammary gland/fat ratios at intervals of, for example, 10%. Therefore, contrast values of undefined breast thicknesses, tube voltages and mammary gland/fat ratios may be calculated by interpolation calculation using values of contrast values in adjacent values for breast thicknesses, tube voltages and mammary gland/fat ratios in the contrast table LUT 2.

The contrasts defined in the contrast table are calculated by simulation. In the present embodiment, in a radiation image, the difference between the signal value of mammary glands included in the breast M and the signal value of fat is defined as the contrast. Actually, since the mammary glands overlap with fat and are contained in the radiation image, in the present embodiment, the difference between the signal value of a radiation image for a case where the mammary gland is present at 50% (that is, the mammary gland/fat ratio is 50%) and the signal value of the mammary gland and the signal value of a radiation image for a case in which a mammary gland having a thickness of 5 mm is 100% present (that is, the mammary gland/fat ratio is 100%) in a background having a mammary gland/fat ratio is 50% is defined as the contrast. Specifically, a subject having a predetermined thickness defined in the contrast table is assumed and that a tissue (mammary gland tissue) with a thickness of 5 mm which is 100% a mammary gland % exists inside the subject. Note that it is assumed that mammary glands are present at 50% within background tissue other than the mammary gland tissue. Then, a signal value QA obtained by X rays transmitted through the mammary gland tissue and a signal value QB acquired by X ray passing through only the background tissue are calculated, and log (QB)−log (QA) is calculated as a contrast value.

In addition, the radiation quality correcting unit 39 acquires second contrast information representing the contrast of the two dimensional image H1. The second contrast information is also calculated based on the first imaging conditions and the thickness of the breast M with reference to the contrast table.

Then, based on the first contrast information and the second contrast information, the radiation quality correcting unit 39 determines the correction amount of the contrast of the projection images Gsi. Here, when the first contrast is A and the second contrast is B, the correction amount is calculated as B/A. Furthermore, the quality correcting unit 39 performs gradation processing on the projection images Gsi based on the determined contrast correction amount, and acquires processed projection images Gsfi which have undergone an image quality correcting process. Here, first, the radiation quality correcting unit 39 corrects reference gradation processing conditions based on the determined contrast correction amount. For example, if the contrast correction amount is 1.35, the slope of a gradation curve, which is a gradation processing condition, is increased by 1.35 times. Then, the radiation quality correcting unit 39 performs gradation processing on the radiation image according to the corrected gradation processing condition, and acquires the processed projection images Gsfi. The image quality correcting unit 33 further analyzes the projection images Gsfi to set normalization processing conditions of the projection image Gsfi, edge emphasis processing conditions, frequency processing conditions, noise filtering processing conditions, dynamic range adjustment processing conditions, and the gradation processing conditions. These processing conditions may be set and further image processing may be performed according to the set image processing conditions. Also, the two dimensional image H1 may be subjected to image processing other than the scattered radiation removing process and the radiation quality correcting process.

The reconstruction unit 34 reconstructs the processed projection images Gsfi to generate tomographic images in which desired cross sectional planes of the breast M are emphasized. Specifically, the reconstruction unit 34 reconstructs the projection images Gsfi using a known back projection method such as a simple back projection method or a filtered back projection method, a shift and add method, or the like to generate a plurality of cross sectional planes Tj, and generates a tomographic image TGj in each of the cross sectional planes Tj.

The image synthesizing unit 35 generates a synthesized two dimensional image H2 using the plurality of tomographic images TGj of the plurality of cross sectional planes Tj of the breast M, which are generated by the reconstruction unit 34. Specifically, a plurality of tomographic images TGj are synthesized to generate a synthesized two dimensional image H2. The synthesized two dimensional image H2 corresponds to the second radiation image. Specifically, the image synthesizing unit 35 adds a plurality of tomographic images TGj generated for each of the plurality of cross sectional planes Tj at corresponding pixel positions, and further enlarges the tomographic images TGj to be of the same size as the two dimensional image H1. Thereby an added tomographic image is generated as a synthesized two dimensional image H2. In this case, it is preferable to geometrically convert the plurality of tomographic images TGj so that the synthesized two dimensional image H2 is obtained at the same source position as that for when the two dimensional image H1 was acquired. The added tomographic image generated in this manner virtually represents the same transmitted image of the breast M as a radiation image acquired by simple imaging.

Note that generation of the synthesized two dimensional image H2 is not limited to the method described above, and any method, such as the method described in PCT Japanese Publication No. 2012-512669 can be used. The method described in PCT Japanese Publication No. 2012-512669 is a method for generating a synthesized two dimensional image H2 using projection images in addition to a plurality of tomographic images TGj.

The subtraction processing unit 36 generates a subtraction image Gsub in which an abnormal part in the breast M is emphasized by calculating a weighted difference value between corresponding pixels of the two dimensional image H1 and the synthesized two dimensional image H2. In the present embodiment, the two dimensional image H1 is acquired by low energy X rays and the synthesized two dimensional image H2 is acquired by high energy X rays. Therefore, by properly weighting among the pixels corresponding to each other within the two dimensional image H1 and the synthesized two dimensional image H2 and computing the difference value, normal blood vessel portions in the breast M are removed. As a result, the subtraction image Gsub is that in which newly formed blood vessels attributable to breast cancer, that is, abnormal portions, are extracted. At this time, the weighted difference value can be easily calculated by aligning the two dimensional image H1 and the synthesized two dimensional image H2 using feature points such as the edges of structures included in the two dimensional image H1 and the synthesized two dimensional image H2.

The display control unit 37 displays the tomographic images TGj on the display unit 3. At this time, the abnormal portion in the subtraction image Gsub may be emphasized in one tomographic image TGj which is being displayed. For example, as illustrated in FIG. 10, in the tomographic image TGj, a color may be assigned to a portion corresponding to an abnormal portion. In FIG. 10, an imparted color is indicated by hatching. In addition, a portion corresponding to the abnormal portion in the tomographic image TGj may be surrounded by a frame or an arrow may be provided to emphasize a portion corresponding to the abnormal portion.

Figure 11:
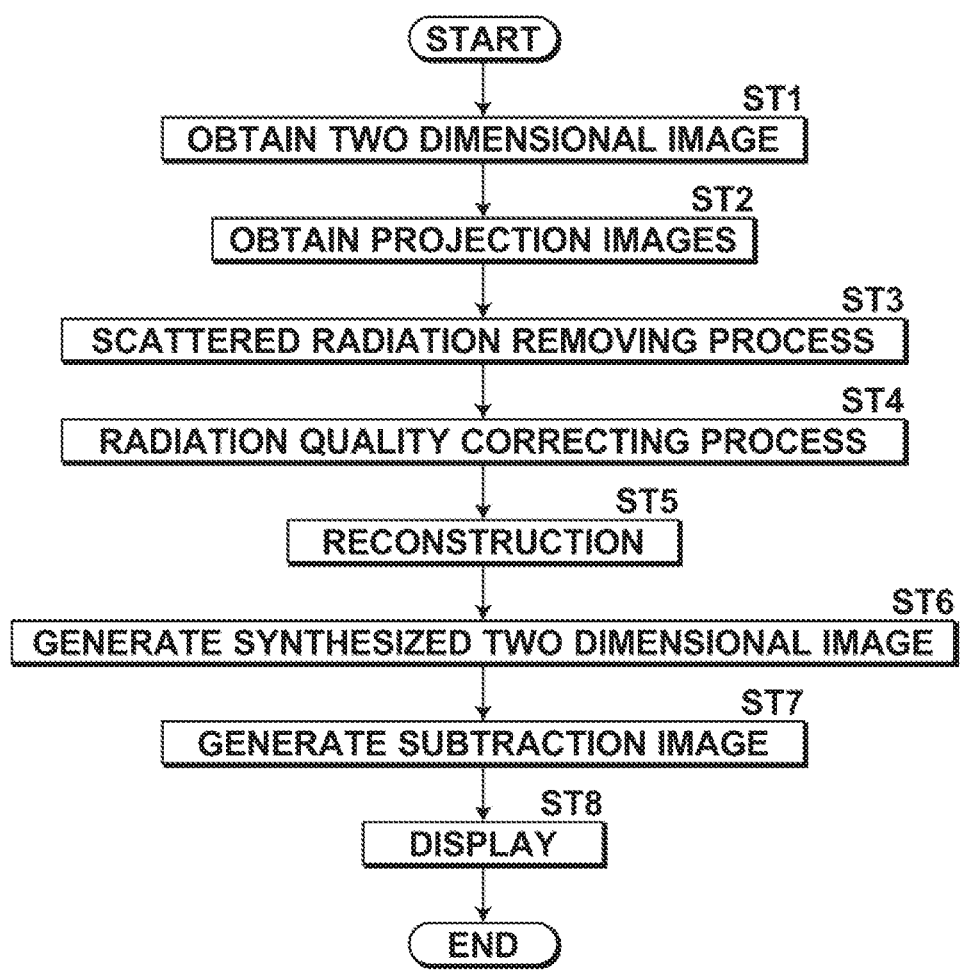
FIG. 11 is a flow chart that illustrates the processes which are executed in the first embodiment.

Next, the processes which are performed by the first embodiment will be described. FIG. 11 is a flow chart that illustrates the processes which are performed by the first embodiment. When the input unit 4 accepts an instruction to start processing by a operator, the X ray source 16 is moved to the first radiation source position Sc and simple imaging is performed under the first imaging conditions, and the first imaging unit 31 Acquires the two dimensional image H1 (step ST1). Next, tomosynthesis imaging is performed according to the second imaging conditions, and the second imaging unit 32 acquires a plurality of projection images Gi (step ST2). Note that the tomosynthesis imaging may be performed prior to simple imaging.

Then, at the time of tomosynthesis imaging, the scattered radiation removing unit 38 of the image quality correcting unit 33 performs the scattered radiation removing process to remove scattered radiation components contained in the X rays transmitted through the breast M from the projection images Gi (step ST3). Furthermore, the radiation quality correcting unit 39 of the image quality correcting unit 33 corrects the contrast between the projected images Gi and the two dimensional image H1, which is caused by the difference between the radiation quality under the first imaging conditions and the radiation quality under the second imaging conditions, and a radiation quality correcting process for correcting the difference is administered on the scattered radiation removing processed projection images Gsi (step ST4), to obtain processed projection images Gsfi.

Next, the reconstruction unit 34 reconstructs the processed projection images Gsfi and the two dimensional image H1 to generate tomographic images TGj for a plurality of cross sectional planes of the breast M (step ST5). Further, the image synthesizing unit 35 synthesizes the plurality of tomographic images TGj to generate a synthesized two dimensional image H2 (step ST6). Subsequently, the subtraction processing unit 36 performs a subtraction process on the two dimensional image H1 and the synthesized two dimensional image H2 to generate a subtraction image Gsub (step ST7), and the display control unit 37 displays the tomographic images TGj with an abnormal portion of the breast M, which is specified by the subtraction image Gsub, emphasized therein on the display unit 3 (step ST8), and the process ends.

As described above, in the first embodiment, a plurality of projection images Gi are reconstructed to generate a plurality of tomographic images TGj, and the combined two dimensional image H2 is generated using the plurality of tomographic images TGj. Here, since the tomographic images TGj are generated from a plurality of projection images Gi, noise is reduced therein compared to the projection images Gi. For this reason, noise within the synthesized two dimensional image H2 is also reduced. Therefore, by performing subtraction processing on the two dimensional image H1 and the synthesized two dimensional image H2, it is possible to generate a subtraction image Gsub having high image quality with reduced noise. In addition, since the synthesized two dimensional image H2 is generated from the plurality of tomographic images TGj, it is possible to reduce the number of imaging operations for generating the subtraction image, thereby reducing the radiation dosage that the breast M is exposed to as the subject of the imaging operations.

In addition, since the image quality correcting process is performed on the projection images Gi in order to compensate for the difference in image quality between the projection images Gi and the two dimensional image H1, the image quality of the projection image Gi is capable of matching the image quality of the two dimensional image H1. Alternatively, it is possible to reduce the difference between the image quality of the projection images Gi and the image quality of the two dimensional image H1 by causing the image quality of the projection images Gi to approach the image quality of the two dimensional image H1. Therefore, the image quality of the tomographic images, and further, the image quality of the synthesized two dimensional image H2, can be improved.

Further, scattered radiation components can be removed from the projected images Gi by administering the scattered radiation removing process on the projection images Gi. In addition, by performing the radiation quality correcting process, the contrast of the projection image Gsi can be caused to be the same as the contrast of the two dimensional image H1. Therefore, the image quality of the tomographic images, and further, the image quality of the synthesized two dimensional image H2, can be improved without being affected by blurring of the image due to scattered radiation and low contrast.

Also, during imaging, how the scattered radiation is generated differs depending on the X ray quality. Therefore, in the case where the image quality correcting process includes the scattered radiation removing process and the radiation quality correcting process, if the radiation quality correcting process is performed first, it is necessary for the radiation quality correcting process to be performed while taking the degree of occurrence of scattered radiation that depends on the radiation quality into consideration. However, it is technically difficult to administer the radiation quality correcting process while taking the degree of occurrence of scattered radiation that depends on the radiation quality into consideration. Therefore, the image quality correcting process is facilitated, by administering the scattered radiation removing process prior to the radiation quality correcting process.

Figure 12:
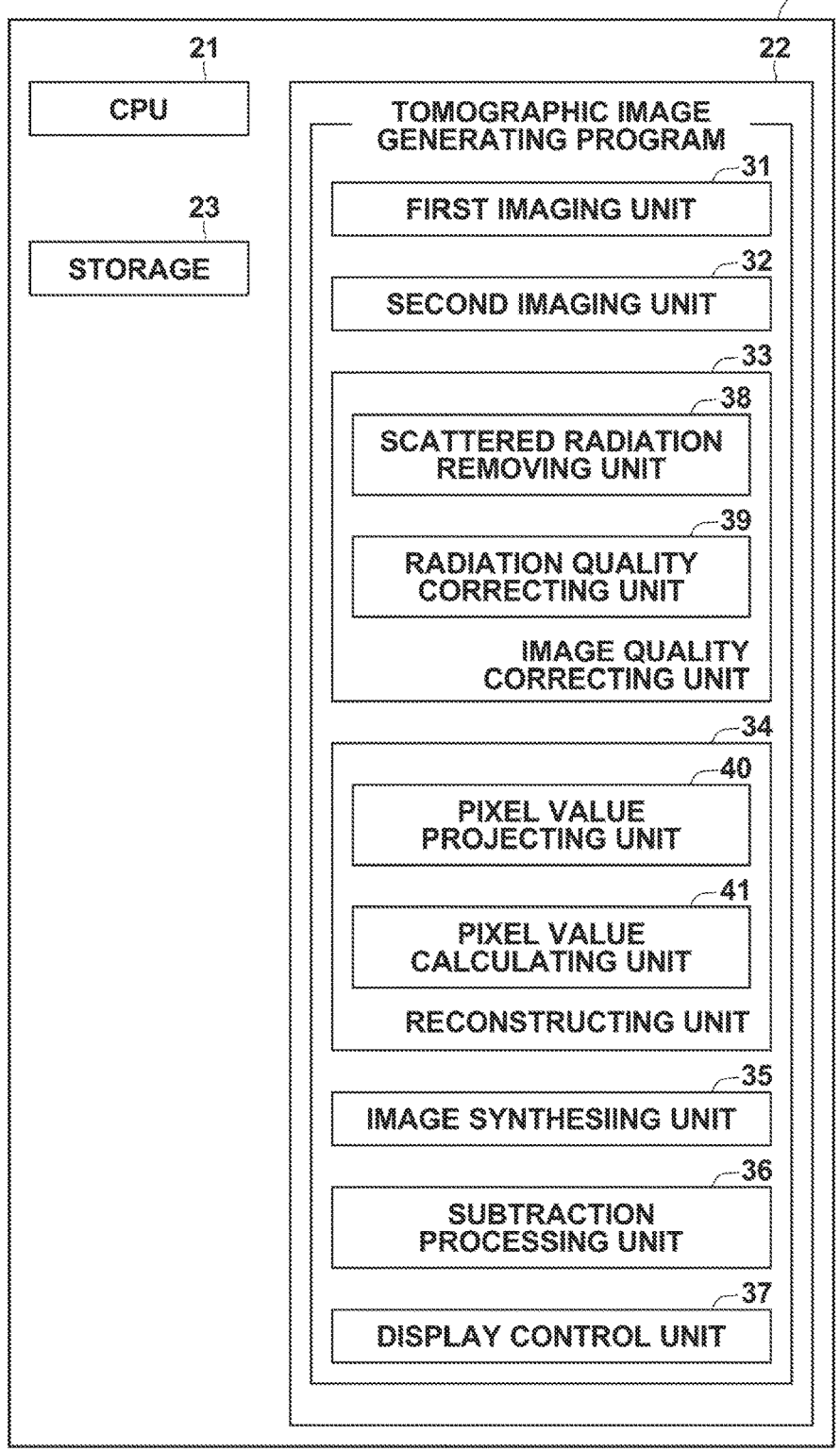
FIG. 12 is a diagram that schematically illustrates the configuration of a radiation image processing apparatus according to a second embodiment, which is realized by installing a radiation image processing program in a computer.

Next, a second embodiment of the present disclosure will be described. FIG. 12 is a diagram that schematically illustrates the configuration of a radiation image processing apparatus according to a second embodiment, which is realized by installing a radiation image processing program in a computer. In the second embodiment, components which are the same as those of the first embodiment are denoted by the same reference numerals, and detailed descriptions thereof will be omitted. As illustrated in FIG. 12, the radiation image obtaining apparatus 1 according to the second embodiment is different from the first embodiment in that the reconstruction unit 34 includes a pixel value projecting unit 40 and a pixel value calculating unit 41.

Figure 13:
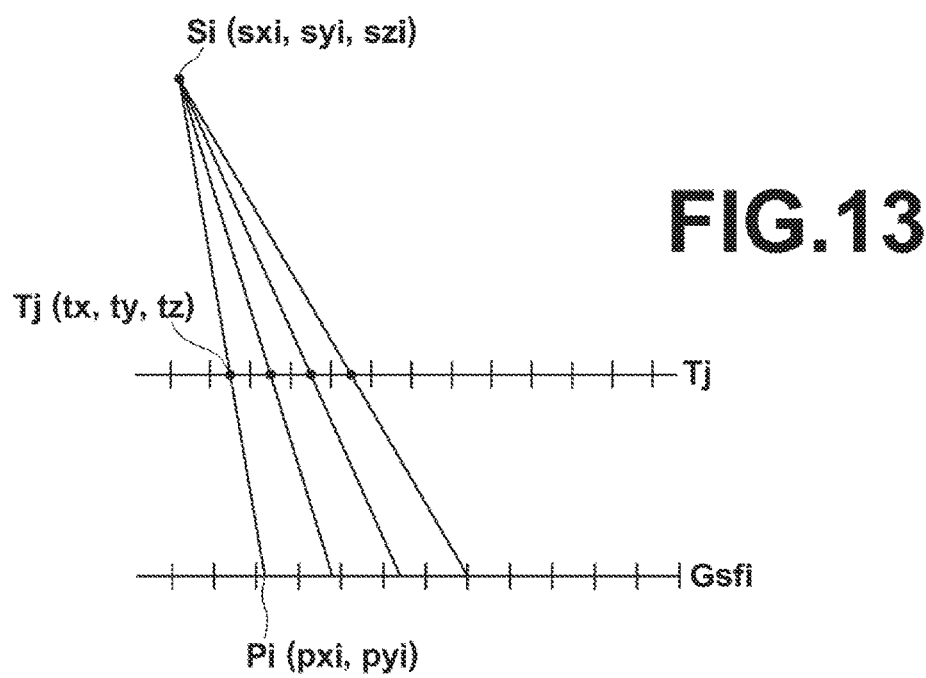
FIG. 13 is a diagram for explaining projection of pixel values in the second embodiment.

The pixel value projecting unit 40 projects pixel values of the plurality of projection images Gsfi onto coordinate positions on desired cross sectional planes of the breast M while maintaining the pixel values of the plurality of processed projection images Gsfi. FIG. 13 is a diagram for explaining projection of pixel values. Note that a case in which a plurality of projection images Gsfi acquired at radiation source positions Si are projected onto desired cross sectional planes Tj (j=1 to m:m is the number of cross sectional planes) of the breast M will be explained with reference to FIG. 13.

Here, the tomographic images generated as will be described later in the projection images Gsfi and the cross sectional planes Tj are composed of a plurality of pixels which are discretely arranged two dimensionally at predetermined sampling intervals. Pixels are arranged at lattice points which are the predetermined sampling interval. In FIG. 13, the short line segments orthogonal to the projection image Gsfi and the cross sectional plane Tj indicate pixel sectioning positions. Therefore, in FIG. 13, the pixel position at the center of the pixel sectioning position is the lattice point. In the second embodiment, as illustrated in FIG. 13, pixel values of a plurality of projection images Gsfi that intersect with a straight line connecting the radiation source position Si and the pixel position on the cross sectional planes Tj are positioned on a corresponding straight line to the pixel value at the pixel position on the cross sectional planes Tj.

Here, if the coordinates of the radiation source position Si are (sxi, syi, szi) and the coordinates of the pixel position on the cross sectional plane Tj are Tj (tx, ty, tz), the coordinates of the coordinate position Pi on the projection image Gsfi (pxi, pyi) are expressed by Formulae (6) below. In the present embodiment, the z axis is set in the direction perpendicular to the detection plane of the radiation detector 15, the y axis is set in the direction parallel to the direction in which the X ray source 16 moves along the detection plane of the radiation detector 15, and the x axis is set in the direction orthogonal to the y axis.

$$Pxi=(tx \times szi - sxi \times tz)/(szi-tz)$$

$$Pyi=(ty \times szi - syi \times tz)/(szi-tz) \qquad (6)$$

Figure 14:
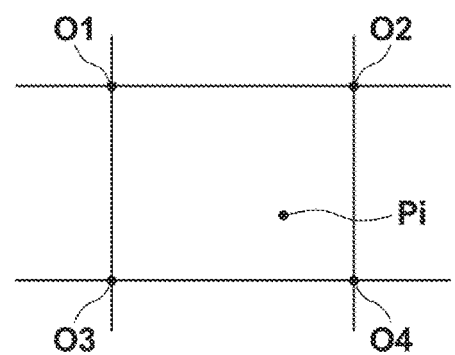
FIG. 14 is a diagram for explaining interpolation of pixel values of a projection image in the second embodiment.

Note that there are cases in which a coordinate position Pi on the projection image Gsfi may not be a pixel position of a projection image Gsfi. For example, as illustrated in FIG. 14, the coordinate position Pi on the projection image Gsfi may be located between the four pixel positions O1 to O4 on the projection image Gsfi. In this case, as illustrated in FIG. 14, an interpolation calculation is performed using the pixel values at the four pixel positions O1 to O4 of the projection image Gsfi at the position closest to the coordinate position Pi, to calculate the pixel value of the coordinate position Pi. Then, the calculated pixel value may be projected onto the pixel position (tx, ty, tz) on the cross sectional plane Tj. As the interpolation calculation, arbitrary methods, such as a non linear bicubic interpolation operation that employs a greater number of pixel values of pixel positions about the periphery of the coordinate position Pi, and a B-spline interpolation operation can be employed, in addition to a linear interpolation operation that weights the pixel values of the four pixel positions according to the distance between the coordinate position Pi and the four pixel positions. As an alternative to the interpolation operation, the pixel value of the pixel position closest to the coordinate position Pi may be employed as the pixel value of the coordinate position Pi.

Figure 15:
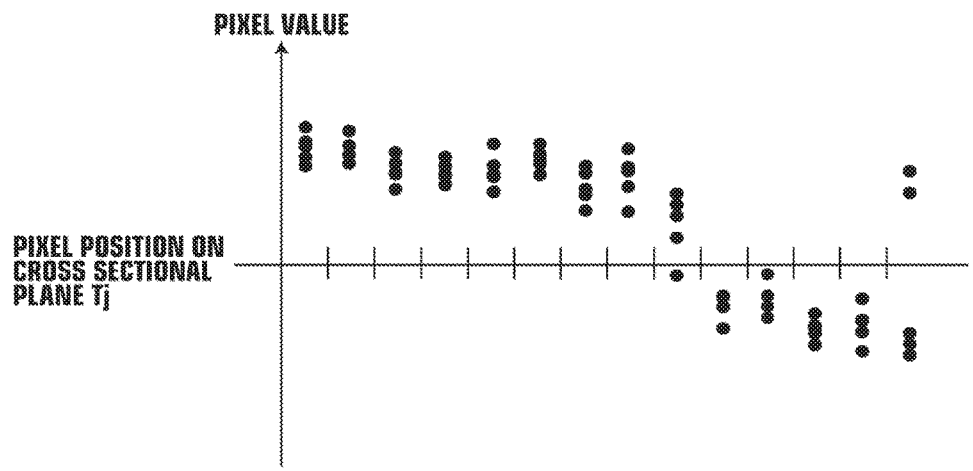
FIG. 15 is a diagram that illustrates pixel values which are projected onto a cross sectional plane.

The pixel value projecting unit 40 projects the pixel values of the plurality of projection images Gsfi on the cross sectional planes Tj for all of the radiation source positions Si. As a result, as illustrated in FIG. 15, n pixel values corresponding to the number of projected images are projected at each pixel position on the cross sectional planes Tj. In FIG. 15, for the sake of explanation, the pixel values of the five projected images Gsfi are projected at each pixel position. In addition, in FIG. 15, FIG. 16, and FIG. 17 to be described later, the short line segments orthogonal to the sectional plane Tj indicates pixel sectioning positions, and the center positions of the pixel separation positions indicates pixel positions which are lattice points.

The pixel value calculating unit 41 calculates each pixel value on the cross sectional plane Tj, to generate a tomographic image on the cross sectional plane Tj. More specifically, the pixel value of a coordinate position of interest is calculated, based on a plurality of pixel values of a plurality of projection images Gsfi projected onto a predetermined range with the coordinate position of interest as a reference. Note that the coordinate position of interest may be pixel positions on the cross sectional plane Tj in some cases. In the second embodiment, the pixel values of a plurality of projection images Gsfi are projected onto the pixel position on the cross sectional plane Tj. However, when calculating the pixel value of the coordinate position of interest, the pixel value of the pixel projected onto the coordinate position of interest may or may not be used. Calculation of the pixel value of the coordinate position of interest will be described below.

The pixel values of the plurality of projection images Gsfi which are projected by the pixel value projecting unit 40 onto the cross sectional plane Tj tend to approximate each other as their locations become closer to each other. Therefore, the pixel value calculating unit 41 performs a process of changing the sharpness so that the pixel values projected on the cross sectional plane Tj are smooth and continuous. In the present embodiment, a filtering process is administered by a smoothing filter on pixel values projected on the cross sectional plane Tj. Specifically, for example, a filtering process using a Gaussian filter is administered on pixel values of pixel positions in a predetermined range such as 3×3 or 5×5 with the coordinate position of interest as the center. As a result, the pixel values are smooth and continuous in the pixels of the coordinate position of interest and the surrounding pixels. Therefore, noise such as quantum noise or the like contained in the pixel values projected on the cross sectional plane Tj of the plurality of projection images Gsfi can be suppressed.

The size of the predetermined range may be stored in the storage 23 as a fixed value. Further, it is also possible to change the size of the predetermined range to arbitrary values by an input by the operator via the input unit. In this case, the value of the size in the predetermined range stored in the storage 23 is rewritten according to the input from the input unit 4 by the operator, and the size of the predetermined range is changed.

Further, by changing the filter size of the Gaussian filter, the degree of smoothing, that is, the degree of noise suppression, can be changed. Specifically, as the filter size is increased and the filtering range centered on the coordinate position of interest is increased, it is possible to further suppress noise. Here, when obtaining the projection images Gsfi, as the amount of X rays that reach the radiation detector 15 is smaller, the noise included in the projection images Gsfi increases. As a result, the noise within the pixel values projected onto the cross sectional planes Tj also increases. In addition, the amount of noise included in the projection images Gsfi varies depending on the X ray quality, that is, whether the X ray is high energy or low energy. Also, the amount of noise included in the projection image Gsfi changes depending on the type of the radiation detector 15 used at the time of imaging. Furthermore, the amount of noise included in the projected images Gsfi varies depending on the presence or absence of a grid at the time of imaging or the type of grid.

Therefore, in the present embodiment, the characteristics of the smoothing filter are changed based on the first and second imaging conditions. For example, in the case of imaging conditions in which the noise included in the projection images Gsfi is large, the filter size is increased such that the noise is further suppressed.

Further, when filtering is performed, if a Gaussian filter is used, there is a possibility that an edge, which is a structure of the breast M included in the tomographic images generated as will be described later, will be blurred. For this reason, for pixels adjacent to the coordinate position of interest, filtering is performed by weighting according to the distances among the pixels and using a bilateral filter weighted by a normal distribution such that weighting becomes smaller as the differences among pixel values is larger. Filtering may also be performed by using a Non-Local Means Filter (non-local averaging filter) that performs weighting based on the similarities among the coordinate position of interest within the cross sectional plane Tj and arbitrary neighboring regions of arbitrary pixels. Thus, since the edge can be preserved while suppressing noise, it is possible to prevent sharpness from decreasing in the tomographic images to be generated as will be described later.

Further, by performing filtering employing a differential filter on the pixel value projected on the cross sectional plane Tj, for example, an edge which has a structure in which the pixel value abruptly changes beyond a predetermined threshold can be detected. In this case, the sharpness may be changed by changing the filter characteristic so as to perform the filtering process along the direction in which the edge is present. For pixel values at the edge boundary, the filtering processing may be performed so as not to use the pixel values existing at positions beyond the edge. As a result, the edges are not smoothed, so that it is possible to prevent sharpness from decreasing in the distribution of pixel values projected onto the cross sectional plane Tj while suppressing noise.

Instead of smoothing or in addition to smoothing, edge enhancement may be performed by administering a process that emphasizes sharpness. In this case, it is preferable to administer the process that emphasizes sharpness along the direction in which the edge is present.

After the filtering is performed in this manner, the pixel value calculating unit 41 performs regression analysis on the pixel values of the projection images Gsfi which are projected on the cross sectional plane Tj, to generate a curved surface representing the tomographic image on the cross sectional plane Tj. Here, in order to simplify the explanation, the regression curved surface is considered as a regression curve. Regression analysis is a statistical method for analyzing multivariate relationships. It is assumed that observed values at an observation point are observed with noise included in a true value. Regression analysis is a method for solving the inverse problem for obtaining the true value at every observation point by a least squares method, a moving average method, regression using a kernel, or the like. In the second embodiment, the coordinate position where the pixel values of the projection images Gsfi are projected onto the cross sectional plane Tj is set as a observation point uk, the pixel values of the projection images Gsfi which are projected onto the observation point uk are set as an observed value qk, the pixel value which is calculated at a coordinate position of interest urn is set as a true value rm and a pixel value rm of the coordinate position of interest urn is calculated by regression analysis.

Figure 16:
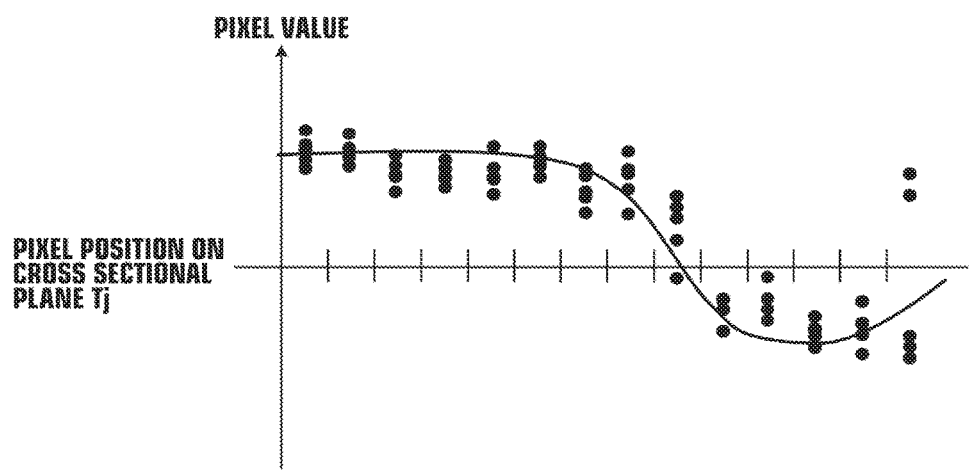
FIG. 16 is a diagram for explaining generation of a regression curve (regression curved surface) that includes outlier values in the second embodiment.

Here, in the case that the least squares method is employed, it is assumed that the distribution of true values follows a function defined by γ parameters a. That is, it is assumed that r=f (u|a1, a2, ... aγ). The function f can be determined by finding parameters a1, a2, ... , aγ that minimize the squared error between the true value and the observed value. Specifically, by determining the parameters of the function f such that the total error of the observed value at the observation point is minimized by the Formula (7) below, the pixel value rm of the coordinate position of interest is calculated and the regression curve (curved surface) is generated. As shown in Formula (8), a weight wk may be set for each observed value qk, and a pixel value rm of the coordinate position of interest um may be calculated by the weighted least squares method to generate a regression curve (curved surface). FIG. 16 illustrates the calculated regression curve (curved surface).

$$r_m = \sum_k \{q_k - f(u_k)\}^2 \quad (7)$$

$$r_m = \sum_k w_k \{q_k - f(u_k)\}^2 \quad (8)$$

Alternatively, in the case that the moving average method is employed, the pixel value of the coordinate position of interest is calculated by a moving average, and a regression curved surface is generated. Specifically, if the regression curved surface is considered as a regression curve in order to simplify the explanation, it is possible to calculate the average value of the pixel values of the projected images Gi projected onto three coordinate positions adjacent to the coordinate position of interest um, that is, coordinate positions uk−1, uk, uk+1, for a pixel value of the coordinate position of interest um. The average value of the pixel values of the coordinate positions uk−1, uk, and uk+1 is calculated as {(qk−1)+qk+(qk+1)}/3 and the calculated average value is stored as the pixel value of the coordinate position of interest urn. Note that a weight may be set for each pixel value. For example, the weight may be set so that the weight decreases as the distance from the coordinate position of interest um increases.

In the case that the regression method using a kernel is employed, a kernel is determined for the observation point uk and the coordinate position of interest urn on the cross sectional plane Tj on which the pixel values of the projection images Gsfi are projected by Formula (9) below. Then, the regression curve (curved surface) is calculated employing the kernel which is determined. In Formula (9), argmin represents that the value of r (um) that minimizes the right side is calculated.

$$r(u_m) = \underset{r(u_m)}{\operatorname{argmin}} \sum_k \{q_k - r(u_m)\}^2 K(u_k, u_m, q_k, q_m) \quad (9)$$

In FIG. 15, out of the five pixel values which are projected onto the rightmost pixel position on the cross sectional plane Tj, two pixel values differ significantly from the pixel values of pixel positions adjacent thereto. When there is a pixel value which is significantly different from the pixel value of the adjacent pixel as described above, when a regression curved surface is generated, the value of the pixel position that includes the outlier differs greatly from that of the pixel position adjacent thereto, as illustrated in FIG. 16. Therefore, when a tomographic image is generated from the calculated regression curved surface as will be described later, artifacts will be generated at the pixel positions which are outliers.

Therefore, the pixel value calculating unit 41 determines pixel values which are significantly different from adjacent pixel values from among the pixel values projected onto the cross sectional plane Tj to be outliers, excludes the pixel values which are outliers, and calculates the pixel value of the coordinate position of interest. For example, the differences between the average value of the pixel values of the pixel positions adjacent to the coordinate position of interest and each of the plurality of pixel values projected onto the coordinate position of interest on the cross sectional plane Tj are calculated. In the case that the difference exceeds a predetermined threshold value, it is only necessary to determine the pixel value as an outlier and exclude the pixel value which is an outlier at the time of regression analysis. Instead of excluding outliers, the weighting of pixel values that are outliers may be reduced.

Figure 17:
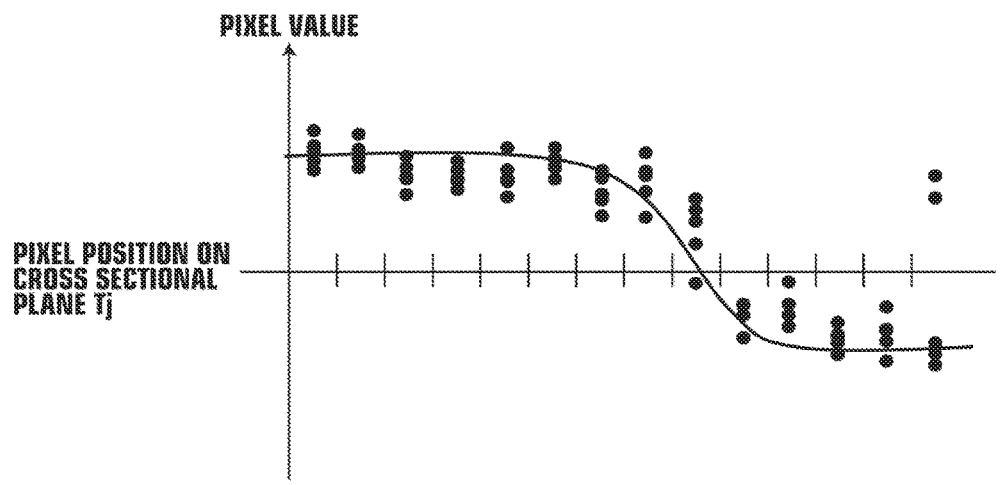
FIG. 17 is a diagram for explaining generation of a regression curve (regression curved surface) from which outlier values are removed in the second embodiment.

If a regression curve (curved surface) is calculated by excluding outliers or reducing the weighting of outlier values in this manner, adjacent pixel positions and values will not change significantly even at pixel positions including outliers, as illustrated in FIG. 17. Thereby, it is possible to prevent artifacts from being included in the tomographic images.

It is also possible to incorporate a process to remove outliers into regression analysis. In the case that the least squares method is employed, the weighted least squares method represented by Formula (8) above may be employed and the weighting of pixel values which are outliers may be set to 0 or decreased. In the case that the moving average method is employed, a weighted average may be obtained, and the weighting of pixel values which are outliers may be set to 0 or decreased.

When a regression curved surface is generated, the pixel value calculating unit 41 samples the regression curved surface at a desired sampling interval to generate a tomographic image. Note that the sampling interval may be stored in the storage 23 as a fixed value. Further, it is also possible to change the sampling interval to an arbitrary value by a command from the input unit 4. For example, if the sampling interval is the same as that of the projection images Gsfi, the tomographic image will have the same resolution as that of the projected images Gsfi, and if the sampling interval is set to be smaller than that of the projected images Gsfi, the tomographic image will have a higher resolution than that of the projected images Gsfi. Conversely, if the sampling interval is set to be greater than that of the projection image Gsfi, it is possible for the tomographic image to have lower resolution than that of the projection images Gsfi. In this case, the value of the sampling interval stored in the storage 23 is rewritten and the sampling interval is changed according to the input from the input unit 4 by the operator. Further, the sampling interval may be adjusted according to the resolution of the display unit 3.

Figure 18:
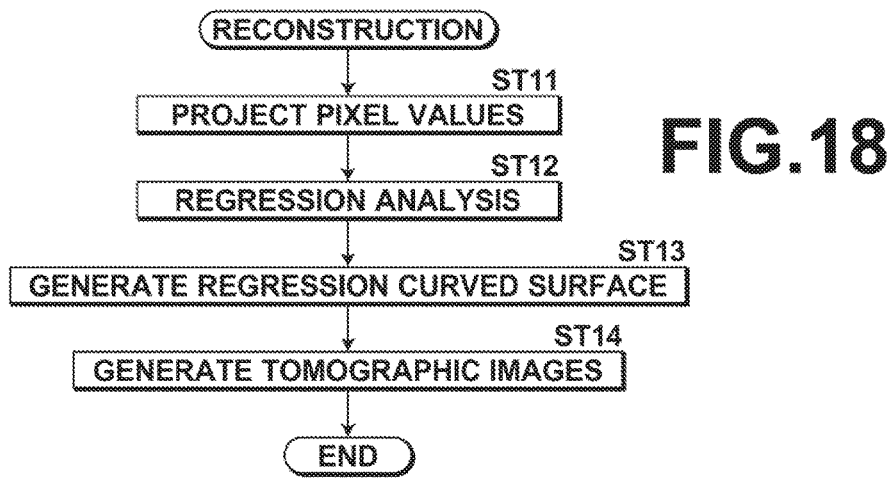
FIG. 18 is a flow chart that illustrates the processes which are executed in the second embodiment.

Next, the processes which are performed in the second embodiment will be described. FIG. 18 is a flow chart that illustrates the processes which are performed in the second embodiment. In the second embodiment, only the reconstruction process differs from the processes which are performed in the first embodiment. Therefore, only the reconstruction process will be described here. In the reconstruction process, the pixel value projecting unit 40 projects the pixel values of the projection images Gsfi onto coordinate positions on a desired cross sectional plane Tj of the breast M while maintaining the pixel values of the projection images Gsfi (step ST11).

Then, the pixel value calculating unit 41 performs regression analysis on the pixel values of the projection images Gsfi which are projected onto the cross sectional plane Tj (step ST 12), and generates a regression curved surface representing the tomographic image on the cross sectional plane Tj (step ST 13). Further, the pixel value calculating unit 41 samples the regression curved surface at a predetermined sampling interval to generate a tomographic image (step ST 14), and the process ends. When a tomographic image is generated on another cross section, the position of the cross sectional plane may be changed and the processes of steps ST11 to ST14 may be performed.

As described above, in the second embodiment, the pixel values of the plurality of projection images Gsfi are projected onto the coordinate positions on the desired cross sectional plane Tj of the breast M, which is the subject, while maintaining the pixel values of the plurality of projection images Gsfi, based on the relationships between the position of the X ray source 16 during imaging with respect to each of the plurality of projection images Gsfi and the position of the radiation detector 15. A tomographic image is generated, by calculating the pixel values of coordinate positions of interest, based on a plurality of pixel values of the plurality of projection images Gsfi which are projected onto the cross sectional plane Tj within a predetermined range with the coordinate positions of interest as a reference by generating a regression curved surface by regression analysis, for example. Therefore, compared to a conventional method of calculating the pixel values of coordinate positions of interest using only the pixel values of the plurality of projection images Gsfi projected onto the coordinate positions of interest, the influence of pixel values about the periphery of the coordinate positions of interest can be taken into consideration. As a result, artifacts can be reduced and a tomographic image with higher image quality can be generated.

In addition, by sampling the regression curved surface at a desired sampling interval and calculating the pixel values of the coordinate positions of interest, it is possible to generate a tomographic image with a desired resolution.

Next, a third embodiment of the present disclosure will be described. The configuration of the tomographic image generating apparatus according to the third embodiment is the same as the configuration of the radiological image processing apparatus according to the second embodiment described above, and only the processes which are performed are different. Therefore, a detailed description of the apparatus will be omitted here. The third embodiment differs from the second embodiment in that the pixel value projecting unit 40 corrects the projection positions of pixel values of the projection images Gi on the cross sectional plane Tj.

Figure 19:
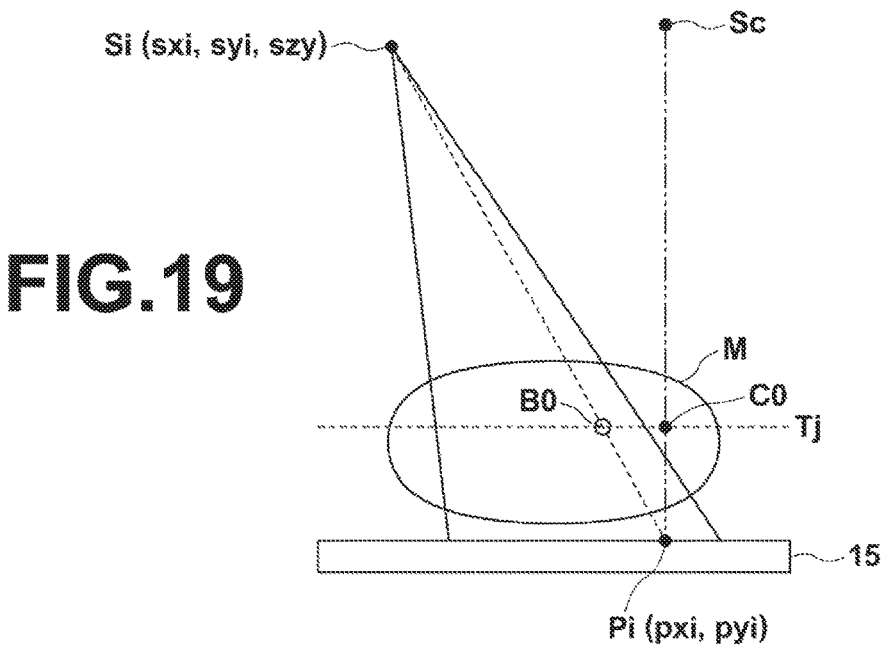
FIG. 19 is a diagram that illustrates the positional relationship between the position of a structure on a cross sectional plane and the position of the structure which is projected onto a radiation detector.
Figure 20:
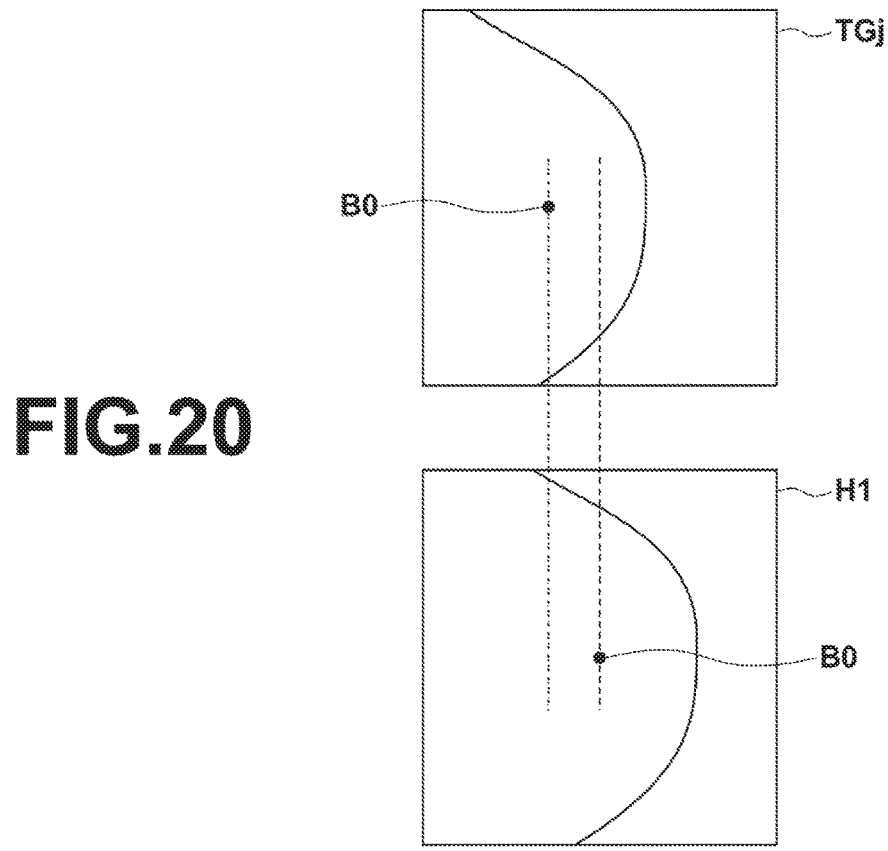
FIG. 20 is a diagram that illustrates the difference in the positions of a structure within a tomographic image and within a radiation image.

Here, as illustrated in FIG. 19, the X rays emitted from the X ray source 16 are cone beams that expand as the distance from the X ray source 16 increases. Further, the surface of the radiation detector 15 from which a projection image Gi is acquired is located farther from the X ray source 16 than the cross sectional plane Tj. Therefore, when the breast M is imaged at the first radiation source position Sc among the plurality of radiation source positions Si, the positions of the mammary glands and a structure B0 such as a calcification contained in the breast M are as shown in FIG. 20. The projection image Gi detected by the radiation detector 15 differs from the tomographic image TGj on the cross sectional plane Tj.

In the case that the two dimensional image H1 is obtained by simple imaging, the position of the X ray source 16 is fixed at the first radiation source position Sc and imaging of the breast M is performed under the first imaging conditions. Therefore, the geometric positional relationship between the projection image acquired at the first radiation source position Sc is the same as that for the two dimensional image H1. For this reason, the position of the corresponding structure B0 differs between the two dimensional image H1 and the tomographic image TGj. In the present embodiment, because the synthesized two dimensional image H2 is generated from the tomographic images TGj in order to obtain the subtraction image Gsub, it is preferable for the position of the corresponding structure B0 in the two dimensional image H1 and the tomographic image to match. Therefore, in the pixel value projecting unit 40 of the third embodiment, the coordinate position within the cross sectional plane Tj onto which the pixel values of the coordinate positions of interest within the projected images Gi are projected are corrected such that the coordinate positions of interest on the projection images Gi match the coordinate positions on the cross sectional plane Tj onto which the pixel values of the coordinate positions of interest are projected, based on the positional relationship between the radiation source position Si during imaging of the projection images Gi and the coordinate position of interest within the projection images Gi.

Correction of the projection position will be described below. As illustrated in FIG. 19, if (sxi, syi, szi) are the coordinates of the radiation source position at the radiation source position Si and Tj (tx, ty, tz) are the coordinates of the structure B0 on the cross sectional plane Tj, coordinates Pi (pxi, pyi) of the projection position of the structure B0 on the radiation detector 15 are represented by Formula (6) above.

Here, if Pi is designated as the coordinate position of interest, the coordinate position of interest Pi will be projected onto the coordinate position Tj (tx, ty, tz) on the cross sectional plane Tj, and the coordinate position on the cross sectional plane Tj onto which the pixel value of the coordinate position of interest Pi is projected can be calculated, by solving Formula for tx and ty, in the case that the coordinate position is not corrected.

Meanwhile, in the case that the X ray source 16 is present at the first radiation source position Sc on a line orthogonal to the detection surface of the radiation detector 15 that passes through the coordinate position Pi (pxi, pyi) as illustrated in FIG. 19, the coordinate position of interest Pi will be projected onto the intersection C0 of a straight line connecting the first radiation source position Sc and the coordinate position Pi, and the cross sectional plane Tj. Thereby, in the tomographic image TGj of the cross sectional plane Tj, the structure B0 is present at the same two dimensional coordinates as those within the projection image Gi, and as a result, the position of the structure B0 within the projection image Gi which is imaged at the first radiation source position Sc and within the tomographic image at the cross sectional plane Tj are matched. Accordingly, a reference radiation source position for projecting the pixel values of the projected images onto the cross sectional plane Tj is changed to the first radiation source position Sc on the straight line orthogonal to the coordinate position onto which the pixel values of the projected images are to be projected, to correct the coordinate position on the cross sectional plane Tj onto which the pixel value of the coordinate position of interest is projected. Here, assuming that the coordinate position of the first radiation source position Sc that serves as a reference for correction is (sxc, syc, szc), the relationship between the corrected coordinate position of interest Pi and the coordinate position (tx, ty) on the cross sectional plane Tj is represented by the Formula (10) below.

$$P_i(px_i, py_i) = \left( \frac{sz_i}{sz_i - tz} \frac{sz_c - tz}{sz_c} tx - \frac{tz}{sz_i - tz} sx_i + \frac{sz_i}{sz_i - tz} \frac{tz}{sz_c} sx_c, \right.$$
$$\left. \frac{sz_i}{sz_i - tz} \frac{sz_c - tz}{sz_c} ty - \frac{tz}{sz_i - tz} sy_i + \frac{sz_i}{sz_i - tz} \frac{tz}{sc_c} sy_c \right) \quad (10)$$

In Formula (10), $(sz_c-tz)/sz_c$ in the first term of the expression that represents each of pxi and pyi represents the enlargement ratio of the coordinate position, and the third term represents the amount of movement of the coordinate position in the x direction and the y direction. Accordingly, by solving the equation (10) for tx and ty, it is possible to calculate the corrected coordinate position on the cross sectional plane Tj on which the pixel value of the coordinate position of interest Pi is projected.

As described above, by correcting the coordinate position on the cross sectional plane Tj onto which the pixel values of the projection images Gi are projected, it is possible to cause the positions of corresponding structures to match among the tomographic images. In addition, the positions of structures such as tumors which are included in the tomographic images can be matched to the positions of structures which are included in the two dimensional image H1. Therefore, because correlation of the pixel values when the synthesized two dimensional image H2 is generated is facilitated, it is possible to generate the synthesized two dimensional image H2 having higher image quality. Also, when generating the subtraction image Gsub from the two dimensional image H1 and the synthesized two dimensional image H2, it is possible to easily align corresponding pixel positions therein.

In each of the embodiments described above, the scattered radiation removing process and the radiation quality correcting process are performed as the image quality correcting processes. Alternatively, only one of the scattered radiation removing process and the radiation quality correcting process may be performed. As a further alternative tomographic images may be generated by performing reconstruction without performing an image quality correcting process.

In each of the embodiments described above, the breast M injected with the contrast agent is subjected to simple imaging and tomosynthesis imaging to generate the subtraction image Gsub. Alternatively, only one of simple imaging of the breast M injected with the contrast agent and tomosynthesis imaging of the breast M injected with the contrast agent may be performed. For example, an image of the breast M prior to injection of the contrast agent may be obtained by simple imaging, and images the breast M following injection of the contrast agent may be obtained by tomosynthesis imaging. As a further alternative, images of the breast M prior to injection of the contrast agent may be obtained by tomosynthesis imaging, and images of the breast M following injection of the contrast agent may be obtained by simple imaging. In this case, the subtraction image Gsub will not be an energy subtraction image, but will be a temporal subtraction image. In addition, in the case that images of the breast M following injection of the contrast agent are obtained by simple imaging and tomosynthesis imaging and a subtraction image Gsub is generated therefrom, a temporal difference will exist between the time when simple imaging was performed and the time when tomosynthesis imaging was performed. Therefore, the spread of the contrast agent can be observed based on the obtained subtraction image Gsub.

In the embodiments described above, the subject is the breast M, but the subject is not limited to being a breast. It goes without saying that any arbitrary part of the human body, such as the chest and the abdomen, may be the subject. In such cases, the distribution of the object thickness is required in order to calculate the scattered radiation content distribution S (x, y) in the scattered radiation removing process described above. The distribution of the subject thickness T (x, y) may be calculated by converting the pixel values of the projected images using a radiation attenuation coefficient value, presuming that the brightness distribution within the projected images substantially matches the distribution of the subject thickness. Alternatively, the thickness of the subject may be measured by employing sensors or the like, or approximated by cuboid or cylindrical models. Note that depending on the portion to be imaged, simple imaging and tomosynthesis imaging may be performed without utilizing a contrast agent.

Hereinafter, the operational effects of the present embodiment will be described.

By administering the image quality correcting processes on a plurality of projection images in order to compensate for differences in image quality between the first radiation image and the second radiation image, the image quality of the second radiation image may match, or approach the image quality of the first radiation image such that the difference in the image quality of the first radiation image and the image quality of the second radiation image can be decreased. Accordingly, the image quality of the tomographic images and further, the image quality of the second radiation image can be improved.

By using at least one of the scattered radiation removing process and the radiation quality correcting process as the image quality correcting process, it is possible to remove the scattered radiation components from the tomographic images or the second radiation image when the scattered radiation removing process is performed. Further, when the radiation quality correcting process is performed, the contrast of the second radiation image can be caused to match the contrast of the first radiation image. Therefore, it is possible to improve the image quality of the tomographic image and further the second radiation image, without being affected by at least one of blur of the image due to the scattered radiation and low contrast.

During imaging, how the scattered radiation is generated differs depending on the X ray quality. Therefore, in the case where the image quality correcting process includes the scattered radiation removing process and the radiation quality correcting process, if the radiation quality correcting process is performed first, it is necessary for the radiation quality correcting process to be performed while taking the degree of occurrence of scattered radiation that depends on the radiation quality into consideration. However, it is technically difficult to administer the radiation quality correcting process while taking the degree of occurrence of scattered radiation that depends on the radiation quality into consideration. Therefore, in the case that the image quality correcting process includes both the scattered radiation removing process and the radiation quality correcting process, the image quality correcting process is facilitated, by administering the scattered radiation removing process prior to the radiation quality correcting process.

The pixel values of the projected images are projected onto desired coordinate positions on the cross sectional plane of the subject based on the positional relationship between the radiation source position at the time that the projection images were obtained and the detection means, while maintaining the pixel values of the projection images. The pixel values of coordinate positions of interest are calculated based on a plurality of pixel values of the projection images projected onto a predetermined range with the coordinate positions of interest on the cross sectional plane as a reference, to generate a tomographic image, The influence of the pixel values about the peripheries of the coordinate positions of interest can be taken into consideration compared to the conventional method in which the pixel value of the coordinate position of interest is calculated using only the pixel values of projection images which are projected onto coordinate positions. As a result, it is possible to reduce artifacts and generate tomographic images having higher image quality, and furthermore, a second radiation image having higher image quality.

Regression analysis is performed to generate a regression curved surface that represents a tomographic image on a cross sectional plane, the regression curved surface is sampled at a desired sampling interval, and the pixel values of pixel positions on the cross sectional plane are calculated. Therefore, it is possible to obtain tomographic images having a desired resolution, and furthermore, a second radiation image can be generated.

When displaying the plurality of tomographic images on the display means, by emphasizing the abnormal part specified by the subtraction image, it is possible to accurately discriminate the abnormal part in the tomographic images.

When a plurality of tomographic images are displayed on the display means, by superimposing the subtraction image and the plurality of tomographic images, it is possible to accurately discriminate the abnormal part in the tomographic images.

What is claimed is:

1. A radiation image processing apparatus comprising:
   a memory configured to store executable instructions; and
   at least one hardware processor configured to execute the executable instructions, which when executed by the at least one hardware processor cause the processor to implement:
     a first image obtaining unit configured to obtain a first radiation image which is imaged by irradiating radiation onto a subject from a first radiation source position under first imaging conditions;
     a second image obtaining unit configured to obtain a plurality of projection images corresponding to each of a plurality of radiation source positions by moving a radiation source relative to a detecting unit and irradiating the subject with radiation from the plurality of radiation source positions under second imaging conditions;
     a reconstructing unit configured to generate a plurality of tomographic images for each of a plurality of cross sectional planes within the subject by reconstructing the plurality of projection images;
     an image synthesizing unit configured to generate a second radiation image employing the plurality of tomographic images;
     a subtracting unit configured to administer subtraction processes on the first radiation image and the second radiation image to generate a subtraction image; and
     an image quality correcting processing unit configured to administer image quality correcting processes that compensate for differences in the image qualities of the first radiation image and the second radiation image, based on differences between the first imaging conditions and the second imaging conditions.

2. A radiation image processing apparatus as defined in claim 1, wherein:
   the image synthesizing unit generates the second radiation image by combining a plurality of tomographic images.

3. A radiation image processing apparatus as defined in claim 1, wherein:
   the image correction processes include at least one of: a scattered radiation removing process that removes scattered radiation components included in radiation which has passed through the subject from the plurality of projection images in the case that imaging is performed employing the second imaging conditions; and a radiation quality correcting process that corrects differences in contrast between the first radiation image and the plurality of projection images, due to differences in the radiation quality of the first imaging conditions and the radiation quality of the second imaging conditions.

4. A radiation image processing apparatus as defined in claim 3, wherein:
   the image quality correcting processes include the scattered radiation removing process and the radiation quality correcting process.

5. A radiation image processing apparatus as defined in claim 4, wherein:
   the image quality correction processing unit administers the scattered radiation removing process before administering the radiation quality correcting process.

6. A radiation image processing apparatus as defined in claim 1, wherein the reconstructing unit comprises:
   a pixel value projecting unit configured to project pixel values of the projection images onto coordinate positions on cross sectional planes of the subject while maintaining the pixel values of the projection images, based on the positional relationship between the radiation source position and the detecting unit at the time of imaging; and
   a pixel value calculating unit configured to generate the tomographic images of the cross sectional planes by calculating the pixel value at a coordinate position of interest, based on a plurality of pixel values of the projection images which are projected within a predetermined range having the coordinate position of interest within the cross sectional planes as a reference position.

7. A radiation image processing apparatus as defined in claim 6, wherein:
   the pixel value calculating unit performs regression analysis on the pixel values of the projection images which are projected onto the cross sectional plane, to calculate the pixel value of the coordinate position of interest.

8. A radiation image processing apparatus as defined in claim 1, wherein:
   the image synthesizing unit corrects the pixel positions of a plurality of tomographic images such that they are those that would be the pixel positions for a case in which radiation is irradiated onto the subject from the first radiation source position, to generate the second radiation image.

9. A radiation image processing apparatus as defined in claim 1, wherein:
   the image synthesizing unit generates the second radiation image such that it is of the same size as the first radiation image.

10. A radiation image processing apparatus as defined in claim 1, further comprising:

a display control unit for displaying the plurality of tomographic images on a display unit.

11. A radiation image processing apparatus as defined in claim 10, wherein:
the display control unit displays the plurality of tomographic images such that an abnormal portion which is specified by the subtraction image is emphasized.

12. A radiation image processing apparatus as defined in claim 10, wherein:
the display control unit displays the subtraction image overlapped with each of the plurality of tomographic images.

13. A radiation image processing apparatus as defined in claim 1, wherein:
at least one of the first radiation image and the plurality of projection images are obtained by imaging operations that employ a contrast agent.

14. A radiation image processing method, comprising:
obtaining a first radiation image which is imaged by irradiating radiation onto a subject from a first radiation source position under first imaging conditions;
obtaining a plurality of projection images corresponding to each of a plurality of radiation source positions by moving a radiation source relative to a detecting unit and irradiating the subject with radiation from the plurality of radiation source positions under second imaging conditions;
generating a plurality of tomographic images for each of a plurality of cross sectional planes within the subject by reconstructing the plurality of projection images;
generating a second radiation image employing the plurality of tomographic images; and
administering subtraction processes on the first radiation image and the second radiation image to generate a subtraction image; and
administering image quality correcting processes that compensate for differences in the image qualities of the first radiation image and the second radiation image, based oil differences between the first imaging conditions and the second imaging conditions.

15. A non transitory recording medium having a radiation image processing program stored therein, the radiation imaging processing program causing a computer to execute the procedures of:
obtaining a first radiation image which is imaged by irradiating radiation onto a subject from a first radiation source position under first imaging conditions;
obtaining a plurality of projection images corresponding to each of a plurality of radiation source positions by moving a radiation source relative to a detecting unit and irradiating the subject with radiation from the plurality of radiation source positions under second imaging conditions;
generating a plurality of tomographic images for each of a plurality of cross sectional planes within the subject by reconstructing the plurality of projection images;
generating a second radiation image employing the plurality of tomographic images; and
administering subtraction processes on the first radiation image and the second radiation image to generate a subtraction image; and
administering image quality correcting processes that compensate for differences in the image qualities of the first radiation image and the second radiation image, based on differences between the first imaging conditions and the second imaging conditions.

* * * * *